US009314276B2

(12) United States Patent
Hess et al.

(10) Patent No.: US 9,314,276 B2
(45) Date of Patent: Apr. 19, 2016

(54) INTERSPINOUS PROCESS IMPLANT AND FUSION CAGE SPACER

(71) Applicant: Spinal Simplicity LLC., Overland Park, KS (US)

(72) Inventors: Harold Hess, Leawood, KS (US); Melissa Frock, Larwill, IN (US)

(73) Assignee: Spinal Simplicity LLC., Overland Park, KS (US)

( * ) Notice: Subject to any disclaimer, the term of this patent is extended or adjusted under 35 U.S.C. 154(b) by 6 days.

(21) Appl. No.: 14/560,006

(22) Filed: Dec. 4, 2014

(65) Prior Publication Data

US 2015/0112387 A1   Apr. 23, 2015

Related U.S. Application Data

(63) Continuation of application No. 12/554,922, filed on Sep. 7, 2009, now Pat. No. 8,945,184.

(60) Provisional application No. 61/209,997, filed on Mar. 13, 2009.

(51) Int. Cl.
| | | |
|---|---|---|
| *A61B 17/70* | (2006.01) | |
| *A61B 17/00* | (2006.01) | |
| *A61F 2/44* | (2006.01) | |
| *A61B 17/56* | (2006.01) | |

(52) U.S. Cl.
CPC ....... *A61B 17/7065* (2013.01); *A61B 17/00234* (2013.01); *A61B 17/7062* (2013.01); *A61B 17/7068* (2013.01); *A61B 17/7074* (2013.01); *A61B 2017/564* (2013.01); *A61F 2/4465* (2013.01)

(58) Field of Classification Search
CPC .... A61B 17/56; A61B 17/70; A61B 17/7065; A61B 17/7067; A61B 17/7068; A61B 17/7071
USPC ............... 606/246–249, 63, 66, 68, 310, 323, 606/326, 327; 623/17.11, 17.16; 411/24–25, 32, 340
See application file for complete search history.

(56) References Cited

U.S. PATENT DOCUMENTS

| | | | | |
|---|---|---|---|---|
| 1,346,578 | A * | 7/1920 | Windsor | 411/340 |
| 4,116,104 | A * | 9/1978 | Kennedy | 411/427 |
| 4,573,844 | A * | 3/1986 | Smith | 411/340 |
| 4,599,086 | A * | 7/1986 | Doty | 606/86 A |
| 4,632,101 | A * | 12/1986 | Freedland | 606/68 |
| 4,721,103 | A * | 1/1988 | Freedland | 606/319 |
| 4,998,936 | A * | 3/1991 | Mehdian | 606/250 |
| 5,098,433 | A * | 3/1992 | Freedland | 606/63 |
| 5,514,180 | A * | 5/1996 | Heggeness et al. | 623/17.16 |
| 5,645,599 | A * | 7/1997 | Samani | 623/17.16 |
| 5,653,761 | A * | 8/1997 | Pisharodi | 606/86 A |

(Continued)

*Primary Examiner* — Eduardo C Robert
*Assistant Examiner* — Michelle C Eckman
(74) *Attorney, Agent, or Firm* — Locke Lord LLP; Scott D. Wofsy; Arpita G. Buesing

(57) ABSTRACT

A spinal implant includes an elongated body dimensioned and configured to function as a spacer, for placement in a target interspinous process space, between two adjacent spinous processes, a distal anchor associated with a distal end of the body, and a proximal anchor mounted for longitudinal movement along the body between a first position spaced apart from the head and a second position approximated with the head, adapted to compress the two adjacent spinous processes, in conjunction with the distal anchor.

2 Claims, 17 Drawing Sheets

(56) References Cited

U.S. PATENT DOCUMENTS

| | | | |
|---|---|---|---|
| 5,836,948 A * | 11/1998 | Zucherman et al. | 606/249 |
| 5,860,977 A * | 1/1999 | Zucherman et al. | 606/249 |
| 5,876,457 A * | 3/1999 | Picha et al. | 623/17.11 |
| 5,904,686 A * | 5/1999 | Zucherman et al. | 606/79 |
| 5,968,098 A * | 10/1999 | Winslow | 623/17.11 |
| 6,017,342 A * | 1/2000 | Rinner | 606/57 |
| 6,045,552 A * | 4/2000 | Zucherman et al. | 606/86 B |
| 6,048,342 A * | 4/2000 | Zucherman et al. | 606/249 |
| 6,068,630 A * | 5/2000 | Zucherman et al. | 606/249 |
| 6,152,926 A * | 11/2000 | Zucherman et al. | 606/279 |
| 6,174,334 B1 * | 1/2001 | Suddaby | 623/17.11 |
| 6,245,108 B1 * | 6/2001 | Biscup | 623/17.11 |
| 6,264,677 B1 * | 7/2001 | Simon et al. | 606/232 |
| 6,402,750 B1 * | 6/2002 | Atkinson et al. | 606/279 |
| 6,451,019 B1 * | 9/2002 | Zucherman et al. | 606/249 |
| 6,514,256 B2 * | 2/2003 | Zucherman et al. | 606/249 |
| 6,610,092 B2 * | 8/2003 | Ralph et al. | 623/17.13 |
| 6,626,944 B1 * | 9/2003 | Taylor | 623/17.16 |
| 6,652,527 B2 * | 11/2003 | Zucherman et al. | 606/249 |
| 6,652,534 B2 * | 11/2003 | Zucherman et al. | 606/102 |
| 6,682,564 B1 * | 1/2004 | Duarte | 623/17.16 |
| 6,695,842 B2 * | 2/2004 | Zucherman et al. | 606/249 |
| 6,709,435 B2 * | 3/2004 | Lin | 606/250 |
| 6,712,819 B2 * | 3/2004 | Zucherman et al. | 606/86 A |
| 6,733,534 B2 * | 5/2004 | Sherman | 623/17.16 |
| 6,743,256 B2 * | 6/2004 | Mason | 623/17.16 |
| 6,746,485 B1 * | 6/2004 | Zucherman et al. | 623/17.16 |
| 6,761,720 B1 * | 7/2004 | Senegas | 606/249 |
| 6,770,096 B2 * | 8/2004 | Bolger et al. | 623/17.16 |
| 6,783,546 B2 * | 8/2004 | Zucherman et al. | 623/17.16 |
| 6,796,983 B1 * | 9/2004 | Zucherman et al. | 606/86 A |
| 6,849,093 B2 * | 2/2005 | Michelson | 623/17.15 |
| 6,860,977 B2 * | 3/2005 | Heinz et al. | 204/298.2 |
| 6,902,566 B2 * | 6/2005 | Zucherman et al. | 606/86 A |
| 6,926,728 B2 * | 8/2005 | Zucherman et al. | 606/190 |
| 6,946,000 B2 * | 9/2005 | Senegas et al. | 623/17.11 |
| 6,949,123 B2 * | 9/2005 | Reiley | 623/17.11 |
| 7,029,473 B2 * | 4/2006 | Zucherman et al. | 606/249 |
| 7,041,135 B2 * | 5/2006 | Michelson | 623/17.11 |
| 7,083,649 B2 * | 8/2006 | Zucherman et al. | 623/17.16 |
| 7,101,375 B2 * | 9/2006 | Zucherman et al. | 606/249 |
| 7,125,425 B2 * | 10/2006 | Foley et al. | 623/17.16 |
| 7,189,234 B2 * | 3/2007 | Zucherman et al. | 606/249 |
| 7,192,446 B2 * | 3/2007 | Shapiro et al. | 623/17.11 |
| 7,201,751 B2 * | 4/2007 | Zucherman et al. | 606/249 |
| 7,217,291 B2 * | 5/2007 | Zucherman et al. | 623/17.15 |
| 7,226,261 B1 * | 6/2007 | Bristol | 411/342 |
| 7,232,464 B2 * | 6/2007 | Mathieu et al. | 623/17.11 |
| 7,238,186 B2 * | 7/2007 | Zdeblick et al. | 623/17.16 |
| 7,238,204 B2 * | 7/2007 | Le Couedic et al. | 623/17.11 |
| 7,320,707 B2 * | 1/2008 | Zucherman et al. | 623/17.14 |
| 7,410,501 B2 * | 8/2008 | Michelson | 623/17.15 |
| 7,423,268 B2 * | 9/2008 | Ren | 250/311 |
| 7,445,637 B2 * | 11/2008 | Taylor | 623/17.16 |
| 7,465,317 B2 * | 12/2008 | Malberg et al. | 623/17.11 |
| 7,465,318 B2 * | 12/2008 | Sennett et al. | 623/17.12 |
| 7,481,840 B2 * | 1/2009 | Zucherman et al. | 623/17.15 |
| 7,497,859 B2 * | 3/2009 | Zucherman et al. | 606/79 |
| 7,503,935 B2 * | 3/2009 | Zucherman et al. | 623/17.15 |
| 7,662,187 B2 * | 2/2010 | Zucherman et al. | 623/17.16 |
| 7,824,429 B2 * | 11/2010 | Culbert et al. | 606/279 |
| 7,918,875 B2 * | 4/2011 | Lins et al. | 606/248 |
| 8,343,190 B1 * | 1/2013 | Mueller et al. | 606/248 |
| 2001/0046429 A1 * | 11/2001 | Gaudron | 411/340 |
| 2002/0015629 A1 * | 2/2002 | Ito | 411/340 |
| 2004/0024463 A1 * | 2/2004 | Thomas et al. | 623/17.16 |
| 2004/0208722 A1 * | 10/2004 | Kuenzel | 411/340 |
| 2005/0129482 A1 * | 6/2005 | Wang | 411/340 |
| 2005/0196420 A1 * | 9/2005 | Zucherman et al. | 424/423 |
| 2005/0245929 A1 * | 11/2005 | Winslow et al. | 606/61 |
| 2006/0036258 A1 * | 2/2006 | Zucherman et al. | 606/90 |
| 2006/0064165 A1 * | 3/2006 | Zucherman et al. | 623/17.11 |
| 2006/0064166 A1 * | 3/2006 | Zucherman et al. | 623/17.11 |
| 2006/0084985 A1 * | 4/2006 | Kim | 606/61 |
| 2006/0089718 A1 * | 4/2006 | Zucherman et al. | 623/17.11 |
| 2006/0182514 A1 * | 8/2006 | Ito | 411/340 |
| 2006/0195102 A1 * | 8/2006 | Malandain | 606/72 |
| 2006/0247634 A1 * | 11/2006 | Warner et al. | 606/61 |
| 2006/0247783 A1 * | 11/2006 | McKay | 623/17.16 |
| 2006/0264938 A1 * | 11/2006 | Zucherman et al. | 606/61 |
| 2006/0264939 A1 * | 11/2006 | Zucherman et al. | 606/61 |
| 2006/0265066 A1 * | 11/2006 | Zucherman et al. | 623/17.11 |
| 2006/0265067 A1 * | 11/2006 | Zucherman et al. | 623/17.11 |
| 2006/0271049 A1 * | 11/2006 | Zucherman et al. | 606/61 |
| 2006/0271194 A1 * | 11/2006 | Zucherman et al. | 623/17.11 |
| 2007/0032790 A1 * | 2/2007 | Aschmann et al. | 606/61 |
| 2007/0055291 A1 * | 3/2007 | Birkmeyer et al. | 606/130 |
| 2007/0093830 A1 * | 4/2007 | Zucherman et al. | 606/61 |
| 2007/0185490 A1 * | 8/2007 | Implicito | 606/61 |
| 2007/0225706 A1 * | 9/2007 | Clark et al. | 606/61 |
| 2007/0270840 A1 * | 11/2007 | Chin et al. | 606/61 |
| 2008/0108990 A1 * | 5/2008 | Mitchell et al. | 606/61 |
| 2008/0147190 A1 * | 6/2008 | Dewey et al. | 623/17.16 |
| 2008/0183211 A1 * | 7/2008 | Lamborne et al. | 606/249 |
| 2008/0243250 A1 * | 10/2008 | Seifert et al. | 623/17.16 |
| 2008/0281359 A1 * | 11/2008 | Abdou | 606/246 |
| 2009/0254185 A1 * | 10/2009 | Dollinger | 623/17.16 |
| 2009/0281626 A1 * | 11/2009 | Farr | 623/17.11 |
| 2010/0057130 A1 * | 3/2010 | Yue | 606/249 |
| 2010/0106191 A1 * | 4/2010 | Yue et al. | 606/249 |
| 2010/0114166 A1 * | 5/2010 | Kohm et al. | 606/247 |
| 2010/0152775 A1 * | 6/2010 | Seifert et al. | 606/249 |
| 2010/0318127 A1 * | 12/2010 | Phan et al. | 606/249 |
| 2011/0066186 A1 * | 3/2011 | Boyer et al. | 606/249 |

* cited by examiner

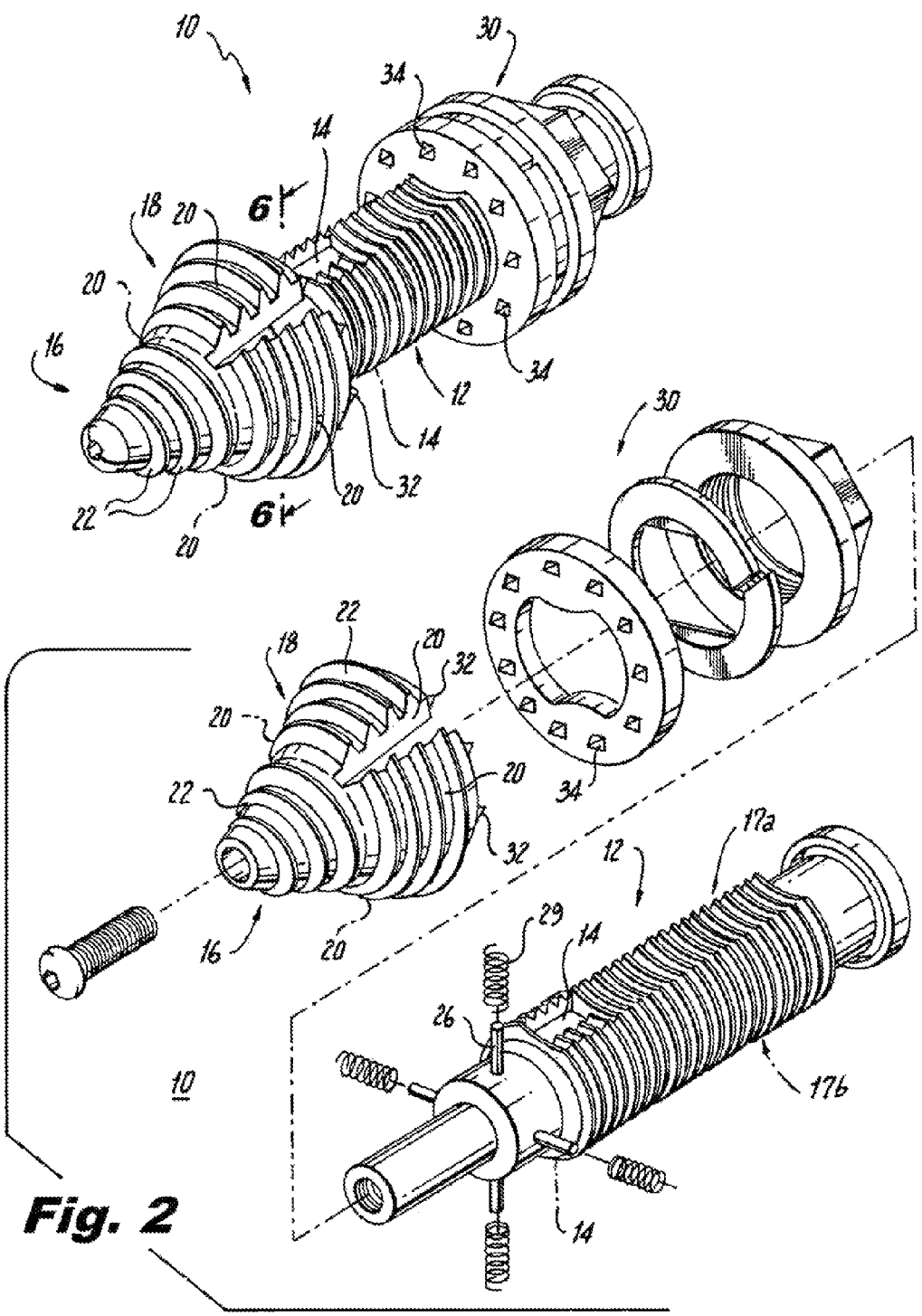

INTERSPINOUS PROCESS IMPLANT AND FUSION CAGE SPACER

CROSS-REFERENCE TO RELATED APPLICATIONS

This application is a continuation of U.S. patent application Ser. No. 12/554,922, filed Sep. 7, 2009, which claims the benefit of and priority to U.S. Patent Application Ser. No. 61/209,997, filed Mar. 13, 2009, these application are incorporated herein by reference in their entirety.

BACKGROUND OF THE INVENTION

1. Field of the Invention

The subject invention is directed to spinal implants, and more particularly, to an interspinous process implant for spinal stabilization, for percutaneous placement in a target interspinous process space, which can also serve as a fusion cage spacer to treat lumbar spinal stenosis.

2. Description of Related Art

The spine consists of a column of twenty-four vertebrae that extend from the skull to the hips. Discs of soft tissue are disposed between adjacent vertebrae. The vertebrae provide support for the head and body, while the discs act as cushions. In addition, the spine encloses and protects the spinal cord, defining a bony channel around the spinal cord, called the spinal canal. There is normally a space between the spinal cord and the borders of the spinal canal so that the spinal cord and the nerves associated therewith are not pinched.

Over time, the ligaments and bone that surround the spinal canal can thicken and harden, resulting in a narrowing of the spinal canal and compression of the spinal cord or nerve roots. This condition is called spinal stenosis, which results in pain and numbness in the back and legs, weakness and/or a loss of balance. These symptoms often increase after walking or standing for a period of time.

There are number of non-surgical treatments for spinal stenosis. These include non-steroidal anti-inflammatory drugs to reduce the swelling and pain, and corticosteroid injections to reduce swelling and treat acute pain. While some patients may experience relief from symptoms of spinal stenosis with such treatments, many do not, and thus turn to surgical treatment. The most common surgical procedure for treating spinal stenosis is decompressive laminectomy, which involves removal of parts of the vertebrae. The goal of the procedure is to relieve pressure on the spinal cord and nerves by increasing the area of the spinal canal.

Interspinous process decompression (IPD) is a less invasive surgical procedure for treating spinal stenosis. With IPD surgery, there is no removal of bone or soft tissue. Instead, an implant or spacer device is positioned behind the spinal cord or nerves between the interspinous processes that protrude from the vertebrae in the lower back. A well-known implant used for performing IPD surgery is the X-STOP® device, which is described in U.S. Pat. No. 6,419,676, the disclosure of which is herein incorporated by reference in its entirety. However, implantation of the X-STOP® device still requires an incision to access the spinal column to deploy the X-STOP® device.

An interspinous process implant placed in a minimally invasive surgical procedure is disclosed in U.S. Patent Application Publication 2008/0243250, which is also incorporated herein by reference in its entirety. This implant functions as a spacer between two adjacent spinous processes, but it is not designed to stabilize the spinous process and can migrate over time.

It would be advantageous to provide an implant for performing IPD procedures that can be percutaneously inserted into the interspinous process space to effectively treat lumbar spinal stenosis by distracting, or maintaining distraction, and sufficiently stabilizing adjacent spinous processes, and thus, adjacent vertebrae.

SUMMARY OF THE INVENTION

In accordance with one aspect, the invention is directed to a spinal implant having an elongated body dimensioned and configured to function as a spacer, for placement in a target interspinous process space, between two adjacent spinous processes, a distal anchor associated with a distal end of the body, and a proximal anchor mounted for longitudinal movement along the body between a first position spaced apart from the head and a second position approximated with the head, adapted to compress the two adjacent spinous processes, in conjunction with the distal anchor.

The proximal anchor can include an axially slideable plate.

The elongated body can be provided with threads at least on a distal portion thereof for facilitating engagement with bony anatomical structures.

The proximal anchor can include a plurality of circumferentially spaced apart distally facing spikes for engaging the spinous processes when the distal anchor and the proximal anchor are approximated.

The body and proximal anchor can be threadedly associated with one another to facilitate longitudinal movement of the proximal anchor along the body between the first and second positions.

The body can be at least partially hollow and include a plurality of openings for permitting tissue ingrowth.

The body can be provided with a tapered head portion, configured to gradually distract the two adjacent spinous processes during insertion therebetween. Similarly, the shape of the body can ease insertion of the implant in-between the adjacent spinous processes after distraction thereof by a separate instrument or instruments.

The distal anchor can include a plurality of radially-deployable blades adapted for engaging adjacent spinous processes. The body can be provided with an internal chamber in which the plurality of radially-deployable blades are stowed prior to deployment thereof. The plurality of radially-deployable blades can be hinged by a common annular pivot member. Alternatively, the plurality of radially-deployable blades can be hinged by a common linear pivot member. The spinal implant can further include an internal plunger adapted for deploying the plurality of radially-deployable blades, by way of a camming mechanism.

In accordance with the invention, the distal anchor can be provided in either a normally expanded or otherwise deployed condition, or alternatively, in a normally contracted or otherwise stowed condition. The term "normally" means that the implant, absent externally-applied forces, maintains that condition.

The distal anchor can include a tapered head, wherein the tapered head has a maximum diameter that is, in its neutral state, greater than a diameter of the elongated body. The tapered head can have a plurality of circumferentially spaced apart proximally-facing spikes for engaging the spinous processes when the head and the anchor are approximated. The tapered head can have a trailing skirt section adapted and configured for movement between a radially expanded condition and a radially compressed condition as the head is inserted between the two adjacent spinous processes. The trailing skirt section of the head can include a plurality of circumferentially spaced apart hinged pleats that are biased into the radially expanded condition. Alternatively, these pleats can be biased in a radially contracted condition. The pleats can be biased by spring elements.

In accordance with another aspect, the invention is directed to a spinal implant having an elongated body dimensioned and configured to function as a spacer, for placement in a target interspinous process space, between two adjacent spinous processes, the body having a tapered head portion, configured to gradually distract the two adjacent spinous processes during insertion therebetween, a distal anchor associated with a distal end of the body, the distal anchor having a plurality of deployable blades adapted to engage a first side of the two adjacent spinous processes, and a proximal anchor mounted for longitudinal movement along the body between a first position spaced apart from the head and a second position approximated with the head, adapted to engage a second side of the two adjacent spinous processes. Alternatively, the body can maintain distraction performed by another instrument, prior to insertion of the implant.

In accordance with still another aspect, the invention is directed to a method of percutaneously performing interspinous process decompression, comprising the steps of providing a spinal implant having an elongated body dimensioned and configured to function as a spacer, for placement in a target interspinous process space, between two adjacent spinous processes, a distal anchor associated with a distal end of the body, and a proximal anchor mounted for longitudinal movement along the body between a first position spaced apart from the head and a second position approximated with the head, adapted to compress the two adjacent spinous processes, in conjunction with the distal anchor, forming an incision in a patient's skin, lateral from a target interspinous process space, in which the implant is to be placed, inserting a stylet through the incision, laterally to the target interspinous process space, using an internal imaging technique, to form an entry path, inserting one or more dilators, sequentially, along the entry path to dilate soft tissues between the incision and the target interspinous process space, inserting a sleeve through the entry path, selecting an implant having a size appropriate for a desired amount of interspinous distraction, inserting the implant, held by an insertion device, through the sleeve, up to the target interspinous process space, and advancing the implant into the interspinous process space.

In accordance with the invention, after the step of inserting the sleeve, a tap can be used. The tap can be a graduated-type tap, the diameter of which increasing toward the proximal end thereof. During rotation of such a tap, threads are cut into the adjacent spinous processes. If the tap is graduated, the adjacent spinous processes are gradually mutually distracted during advancement of the tap. Further, based on the distance the tap advances through the target interspinous process space, the surgeon can determine the size of the implant to insert. In such an arrangement, the subject implant maintains distraction performed by the tap, and does not necessarily perform distraction.

The advancing step can include rotating the implant along a longitudinal axis thereof, to effect axial advancement of the implant by way of threads formed on an outer surface thereof.

BRIEF DESCRIPTION OF THE DRAWINGS

So that those skilled in the art to which the subject invention relates will readily understand how to make and use the interspinous process implant of the subject invention without undue experimentation, embodiments thereof will be described in detail herein below with reference to certain figures, wherein:

FIG. 1 is a perspective view of an interspinous process implant in accordance with a first exemplary embodiment of the invention;

FIG. 2 is an exploded view of the implant of FIG. 1, illustrating the components thereof;

DETAILED DESCRIPTION

Figure 3:
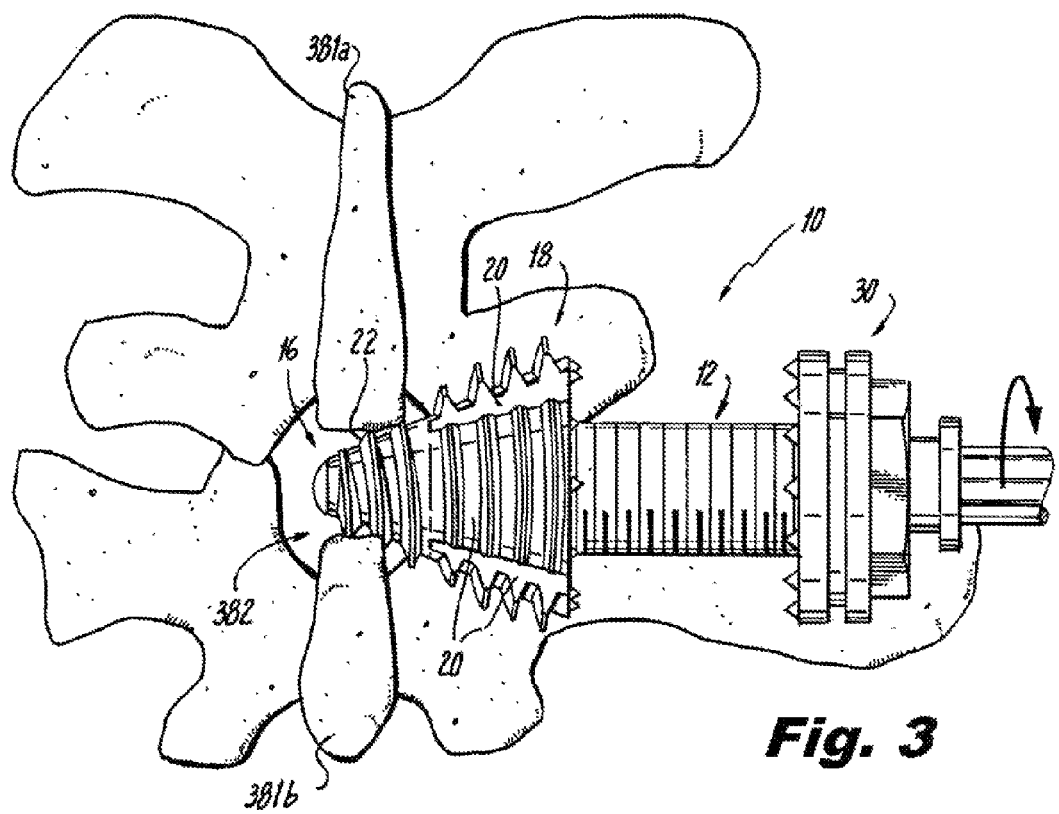
FIG. 3 is a dorsal (rear) view of the implant of FIGS. 1-2, illustrating the implant during installation into a target interspinous process space, prior to compression of a distal end portion thereof.

With reference to FIGS. 1-6, there is illustrated an interspinous implant constructed in accordance with a preferred embodiment of the subject invention and designated generally by reference numeral 10. The implant 10 is particularly well adapted for use in performing minimally invasive surgical procedures for treating spinal stenosis, including, for example, interspinous process decompression (IPD).

It is envisioned however, that the implant 10 of the subject invention can be used in other spinal procedures as well, including, but not limited to as an adjunct to spinal fusion procedures, or as a spinal stabilization device. Those skilled in the art will readily appreciate from the following description that the interspinous process implant of the subject invention is well adapted for percutaneous insertion, and thus overcomes many of the drawbacks of prior art devices presently used in IPD procedures. That is, the implant 10 is dimensioned and configured for introduction and placement through a small skin incision rather than in an open surgical procedure involving a cut down of tissue, as will be described in more detail hereinbelow.

The interspinous process implant 10 includes an elongated threaded body portion 12 which can be configured as a solid element or alternatively can be at least partially hollow, and which may include a plurality of longitudinal openings 14 to permit insertion of demineralized bone or another type of osteogenesis-promoting substances or fusion adjunct material, and also promote the ingrowth of bone. The implant 10 further includes a tapered or conical head portion 16, which is associated with a distal end of the body portion 12. The head portion 16 can be dimensioned and configured to progressively distract two adjacent spinous processes 381a and 381b as the implant 10 is advanced therebetween. It is to be understood, however, that the head portion 16 facilitates insertion of the implant, when distraction is initially performed by a separate instrument. It is also to be understood that the elongated body portion 12 can alternatively be provided without threads, in accordance with an alternative aspect of the invention.

The head portion 16, and with other embodiment set forth herein, tapers axially inwardly, by an angle between about 5 degrees and about 65 degrees, with respect to a longitudinal axis of the implant 10. In accordance with one aspect of the invention, this angle is between about 15 and about 45 degrees. In accordance with another aspect of the invention, this angle is between about 25 and about 35 degrees. In accordance with still another aspect of the invention, this angle is about 30 degrees. It is to be understood however, that this angle is not limited to the foregoing ranges.

The head portion 16 can be attached to the body portion in any suitable manner, including mechanical fasteners, mechanical interlock, welding or the like. In the illustrated embodiment, an axial screw element is provided, although an internal threaded connection can be provided, for example.

The tapered head 16 of implant 10 includes a distal anchor portion configured as a trailing skirt section 18. The skirt section 18, as embodied, is a dynamic structure formed from a plurality of circumferentially spaced apart pleats 20. The pleats 20 can be hinged, and generally arcuate in configuration. Hinging can be accomplished by way of a defined line of weakness in the material, so as to form a "living hinge," or alternatively can be a conventional hinge with a separate pivot. Alternatively still, the necessary deflection of the pleats 20 can be accomplished without a defined hinge, utilizing only the cumulative bending of the pleats 20 along their length. Further, the pleats 20 can be embodied in shapes other than those having an arcuate configuration, such as a generally rectangular parallelepiped, for example.

In accordance with one preferred aspect, the head portion 16 and trailing skirt section 18 have helical threads 22 so as to ease progressive advancement of the head portion 16 and skirt section 18 between the two adjacent bony spinous processes 381a and 381b during insertion therethrough. When applied with a rotational force during insertion, the threads 22 serve to draw the implant 10 into the target interspinous process space 382, defined by the adjacent spinous processes 381a, 381b. It is envisioned that the helical threads 22 can be any of a variety of suitable forms, such as, for example, cutting threads or box threads. However, it is also envisioned and well within the scope of the subject disclosure that the tapered head portion 16 and skirt section 18 can be provided without any threads. Further, an integral tap chamfer can be incorporated into the threads, if so-desired. In embodiments in which no threads are provided, the head portion 16 of the implant 10 can be advanced between the two adjacent spinous processes 381a and 381b by application of a generally axially directed force.

Figure 5:
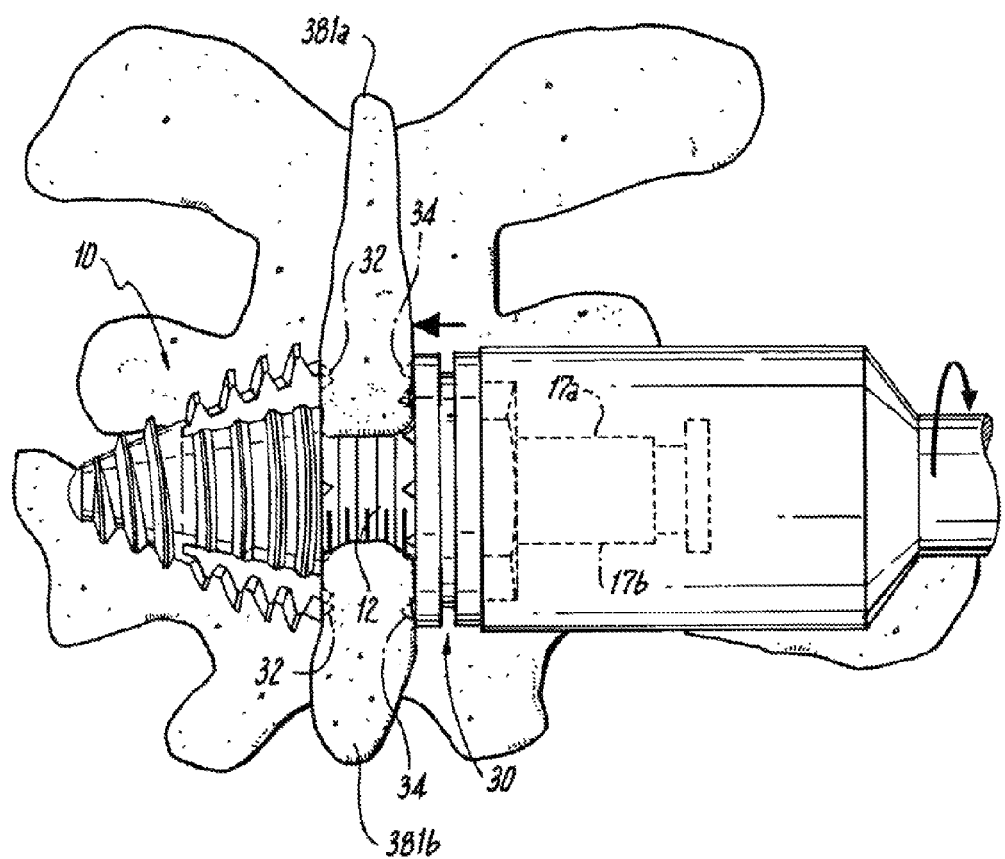
FIG. 5 is a dorsal view of the implant of FIGS. 1-2, illustrating the implant in final position in the target interspinous process space, with a proximal anchor urged distally engaging a proximal surface of adjacent spinous processes, and the proximal end portion engaging distal surface of the adjacent spinous processes.
Figure 6:
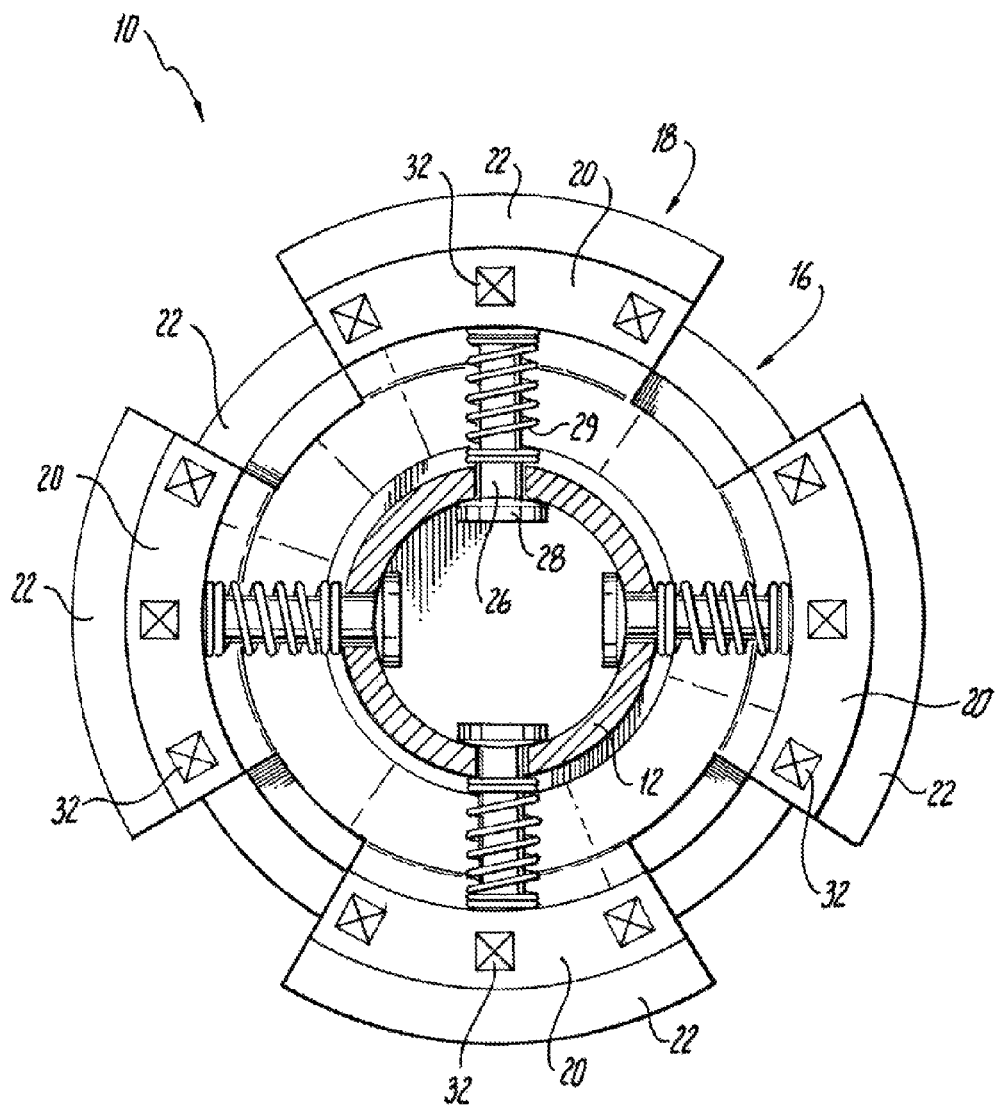
FIG. 6 is a cross-sectional view of the implant of FIG. 1, taken along line 6-6 of FIG. 1, illustrating details of the distal end portion thereof.

As best seen in FIG. 6, each of the arcuate pleats 20 of the skirt section 18 are biased into a radially expanded condition shown in FIG. 1 by coiled biasing springs 25. The coiled biasing springs 25 are supported on guide pins 26 that are retained in body portion 12 by heads 28. The heads 28 of the guide pins 26 act to limit the extent to which the arcuate pleats 20 of skirt section 18 can extend. It is envisioned that alternative biasing mechanisms can be used to bias the pleats 20 into an expanded condition, including but not limited to a provision of elastic material, such as an elastomer. Such a material can be a bio-compatible silicone, for example. As explained in more detail below, the pleats 20 are adapted and configured for movement between a (first) radially expanded condition shown in FIGS. 1-3 and 5 and a (second) radially compressed condition shown, for example, in FIG. 4. If desired, a sheath (not illustrated) can be provided over the structure of the head portion 16, such as a thin layer of a biocompatible elastomer, to maintain a continuous surface while permitting flexibility between the pleats. Alternatively, webs or similar elements can be provided between adjacent pleats 20.

The implant device 10 further includes a proximal anchor portion 30 that is operatively associated with the threaded body 12 in such a manner so as to enable the longitudinal movement of the anchor portion 30 along the length of body 12 between a first position, spaced from the head portion 16 (e.g., FIG. 3) and second position, approximated with the head portion 16 (e.g., FIG. 5). It is envisioned that the operative connection between the body portion 12 and the proximal anchor 30 can be accomplished in a variety of ways including a direct threaded engagement between the proximal anchor 30 and the body 12 or through the use of a captured threaded nut that permits the proximal anchor 30 to translate longitudinally along the threaded body portion 12 without rotating about the axis of the body portion 12, such as by providing one or more interfacing flat regions 17a, 17b.

With reference to FIGS. 1-6, the proximal surfaces of the arcuate pleats 20 of the trailing skirt section 18 can be provided with proximally-directed spikes 24 adapted and configured to engage the bony anatomy of the spinous processes 381a and 381b, when the head portion 16 and the anchor portion 30 are mutually approximated about the spinous processes 381a and 381b. Similarly, the distal surface of the proximal anchor 30 can include a plurality of circumferentially spaced, distally facing spikes 34 for engaging the bony spinous processes 381a and 381b when the head portion 16 and the anchor portion 30 are mutually approximated into the position shown in FIG. 5. The spikes 34, or any spikes described herein in connection with any embodiment of the invention are not limited to any particular shape, but can be generally conical, pyramidal or tetrahedral, for example. Alternatively, the spikes can be truncated versions of such shapes.

Figure 4:
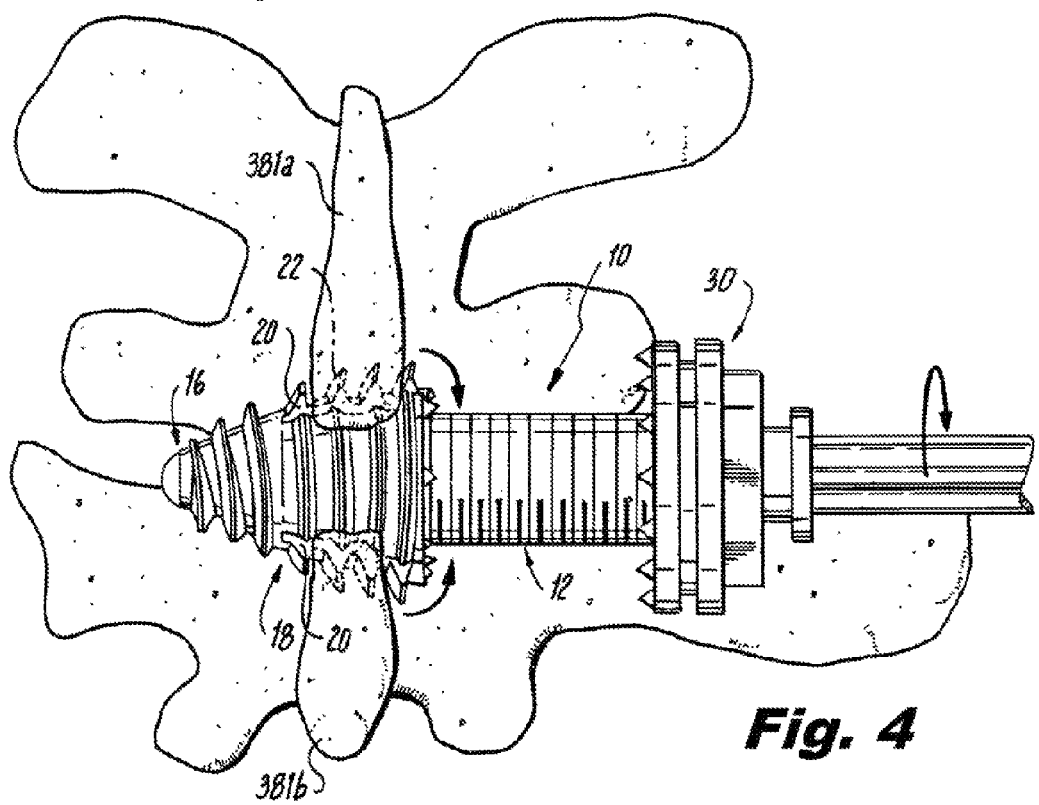
FIG. 4 is a dorsal view of the implant of FIGS. 1-2, illustrating the implant during installation into a target interspinous process space, during compression of the distal end portion thereof.

In use, as the head portion 16 is inserted between the two adjacent spinous processes 381a and 381b, as shown in FIG. 4, the pleats 20 of the skirt section 18 are urged into a compressed condition, against the bias of the coiled springs 25, or alternative biasing elements. In accordance with the invention, the pleats 20 can compress so as to not extend beyond the diameter of the body 12, if necessary. Once the skirt section 18 is beyond the distracted spinous processes 381a, 381b, the pleats 20 are urged back into their normally expanded position under the bias of the springs 25. The implant 10, alternatively, can be inserted following insertion of a separate instrument, such as a tap or other distractor, in which case the implant 10 does not necessarily cause distraction during insertion thereof, but rather maintains distraction.

In accordance with another aspect of the invention, the head portion 16 can be provided and inserted in a collapsed state, and expanded when the implant 10 is placed in the desired position. Expansion of the head portion 16 can be achieved by way of an internal cam mechanism, as described in connection with the embodiments described below. In such an arrangement, an outwardly biasing member can be eliminated, while the heads 28 of the guide pins 26 follow an internal moveable cam, for example. It may be desirable in such an arrangement to provide inwardly-biasing elements (e.g., springs placed within the body 12, between the body 12 and the pin heads 28, if the structure of the head portion 16 alone is not sufficient to maintain a collapsed condition of the head portion 16. The reader will appreciate that any implant constructed in accordance with the invention can be provided in a normally deployed condition, or a normally collapsed condition.

Thereafter, the proximal anchor 30 is moved into approximation with the head portion 16, as shown in FIG. 5. Once approximated, the head portion 16, having a distal anchor composed of the pleats 20, and the proximal anchor 30 compress the spinous processes 381a and 381b therebetween and the spikes 24, 34 on each component secure the implant 10 against unintentional migration. The resulting construct serves to stabilize spinous processes 381a, 381b of the target interspinous process space 382, while at the same time the body portion 12 acts as a spacer between the spinous processes 381a and 381b to decompress tissues between the respective adjacent vertebrae.

The body 12, as with any of the other embodiments described herein can be provided with the following dimensions, but are not limited thereto. The body portion 12 is dimensioned and configured for threaded placement between the spinous processes of symptomatic disc levels. In this regard, it is envisioned that the outer diameter of the implant 10 can range from about 8.0 mm to about 16.0 mm, with the thread depth being about 1.0 mm. The threads on the body portion 12 of the implant 10 can be configured so that the implant is self-tapping to ease insertion of the implant into the interspinous process space, as described below. As mentioned, the implant 10, as with any implant in accordance with the invention, can be provided with or without threads, as desired or required.

The components of the implant 10, or any implant constructed in accordance with the invention can be formed out of similar or identical materials to one another. For example, polymeric materials, such as PEEK, alloys, such as titanium alloys or shape-memory alloys, such as Nitinol, ceramic and/or composite materials can be used, as desired or required. However, it is specifically envisioned that the components of the implant 10 can be formed from different materials from one another. For example, the body 12 can be formed from a polymeric material, such as PEEK, while the head portion can be formed of an alloy, such as a titanium alloy or a shape-memory alloy, such as Nitinol. Ceramic and/or composite materials can additionally or alternatively be used, as desired or required.

Referring now to FIGS. 7-13, there is illustrated another embodiment of the implant of the subject invention, which is designated generally by reference numeral 100. Implant 100 is similar to the previously described implant 10 in that it includes an elongated threaded body portion 112, a tapered head portion 116 at the distal end of the body portion 112 and a proximal anchor portion 130 adapted for longitudinal movement along the length of the body portion 112 between a first portion spaced from the head portion 116 and a second position approximated with the head portion 116.

Implant 100 differs from implant 10 in the manner in which the distal end portion thereof engages the adjacent anatomy (spinous processes 381a, 381b). In accordance with one aspect, instead of having a plurality of outwardly biased pleats (20) as a distal anchor portion, the head portion 116 includes a plurality of circumferentially spaced apart deployable blades 120 that are mounted for pivotal movement about a pivot ring 123, within a bore 150 of the implant 100. In particular, the blades 120 are mounted for movement between a first, stowed position shown in FIG. 7, retracted within the head portion 116 and a second, deployed position shown in FIG. 8, projecting radially outwardly from the head portion 116. The body 112 of the implant 110 is provided with apertures 115, corresponding to each blade 120 provided.

Movement of the blades 120 between the retracted and deployed positions is accomplished, at least in-part, through actuation by an internal plunger 126. More particularly, the surfaces of the head 128 of the plunger 126 act as a cam, and cooperate with inner cam surfaces 140 formed on each of the blades 120. As the plunger head 128 moves distally, cam surfaces 140 of the blades 120 follow the outer surface of the plunger head 128, and urge the blades 120 radially outwardly.

As illustrated, four orthogonal blades 120 are provided, although it is to be understood that any practicable number thereof can be provided, including but not limited to a total of one, two, three, four, five, six, seven, eight, nine or ten blades 120, for example.

The blades 120 and their annular pivot ring 123 are mutually connected within the bore 150 of the body 112, thus forming a subassembly 119. The subassembly 119 can be provided in an axially fixed location along the longitudinal axis of the implant 100, or alternatively can be configured to permit limited axial movement of the subassembly 119.

In one aspect, the blades 120 are fitted to the pivot ring 123, which is in-turn, positionally constrained to, or alternatively integrally formed with, the inner wall 152 of the bore 150. Securement of the axial position of the pivot ring 123 to the wall 152 can be facilitated in any suitable fashion, which may depend on the precise material selection. Mechanical connections can be utilized, for permitting snap or press fitting thereof, for example. For example, one or more stops in the form of protrusions, or alternatively grooves 154, can be provided in the bore 150. With such features, the pivot ring 123 can be captured and its axial position fixed. In this regard, the pivot ring 123 can be configured as a "split ring" or as an otherwise circumferentially compressible member. As such, the subassembly 119 can be inserted axially from the proximal end 117 of the body 112, through the bore 150, and moved toward the distal end of the implant 100. Such engagement can be either permanent or temporary, depending on the precise implementation thereof. Alternatively or additionally, to achieve permanent positioning, the ring 123 can be permanently attached, such as by welding, to the inner wall 152 of the bore 150, provided that compatible materials are used.

If repositionability of the subassembly 119 is desired, the relative size and configuration of protrusions and/or grooves can be such that the pivot ring 123 is releasably captured by such features (e.g., groove 154), and can be removed therefrom upon application of sufficient force. In this regard, the pivot ring 123 includes inherent mechanical properties including elasticity or stiffness (i.e., spring rate), frictional properties and the like, which depend on the material being used. If dimensioned and implemented suitably, the subassembly 119, including the blades 120 and the pivot ring 123 can be axially positioned at any stage by way of such a feature.

Figure 7:
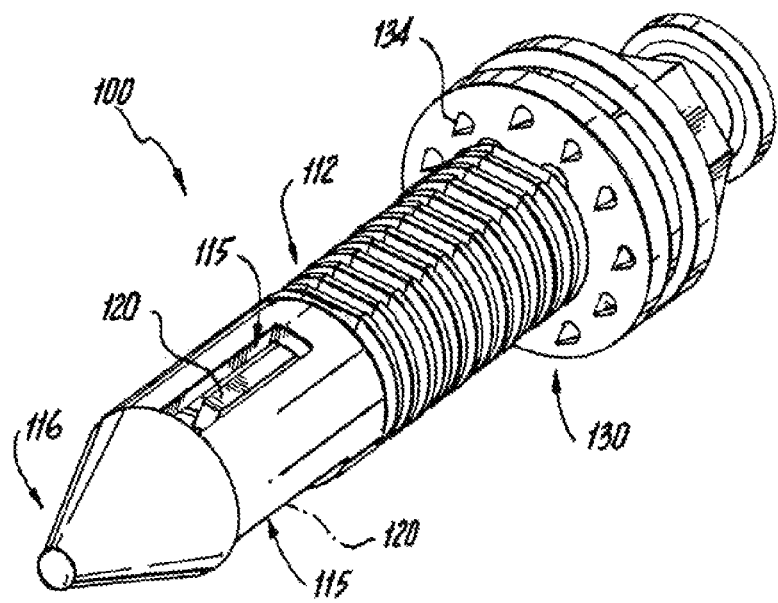
FIG. 7 is a perspective view of an interspinous process implant in accordance with a second exemplary embodiment of the invention, showing distal anchor elements in a stowed position.
Figure 8:
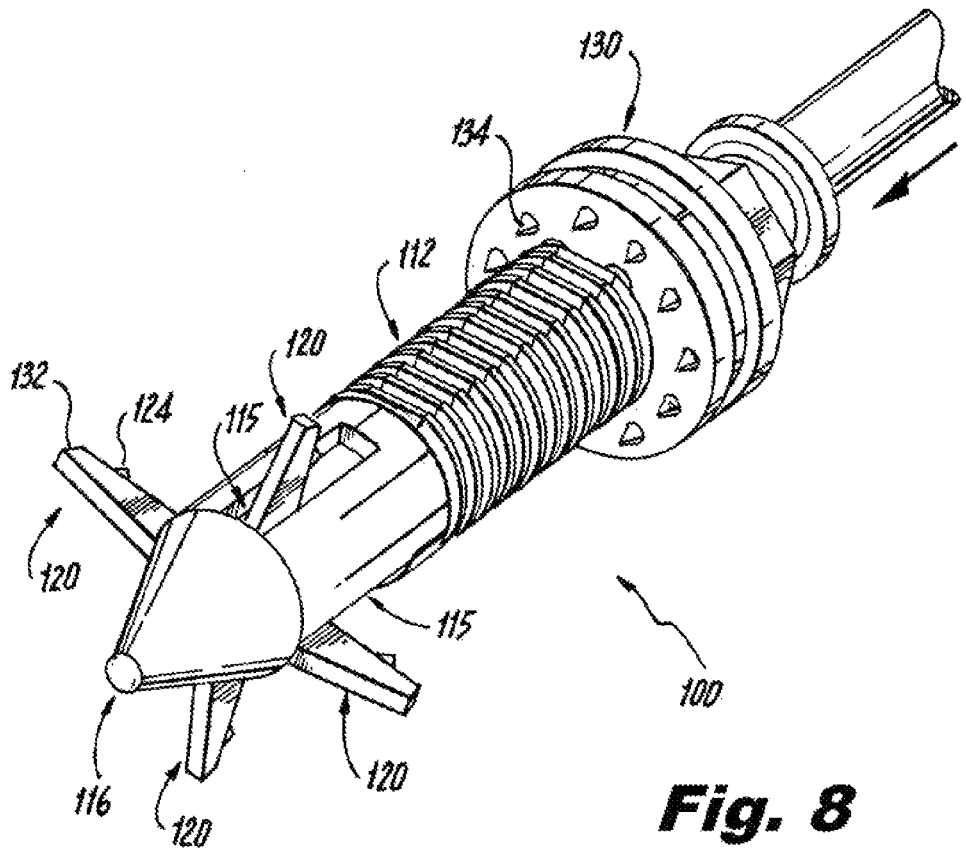
FIG. 8 is a perspective view of the implant of FIG. 7, showing the distal anchor elements in a deployed condition.

As shown in FIG. 7, the blades 120 can be stowed prior to placement of the implant 100. To inhibit unintended pivoting of the blades 120 about the pivot ring 123, which could interfere with the insertion process, a stowed configuration of the subassembly 119 can permit the radially outer ends 132 thereof to be rotated inward, through the apertures 115, and into the bore 150 of the implant 100. The subassembly 119 can then be moved proximally, bringing the blades 120 fully within the bore 150, and capturing their radially outer ends 132 within the bore 150. A positioning feature, such as a groove (e.g., 154) for example, can correspond with this stowed position and maintain the axial position of the subassembly 119 until deployment of the blades 120 is desired. At that time, the plunger 126 can be urged distally, pushing the subassembly 119 to an axial position in which the blades 120 are free to rotate about the pivot ring 123 and through the apertures 115, which can be accomplished by way of movement of the plunger 126 in connection with the cam surfaces 140 of the blades 120, as described above.

Optionally, the subassembly 119 can be configured to travel axially to the distal end of the bore 150, at which position the outer surfaces of the blades 120 abut the inner end face 152 of the bore 150. Such positioning advantageously inhibits eversion or overextension of the blades 120 from a deployed position in which they are configured to engage the target spinous processes 381a, 381b (e.g., FIGS. 10-13).

In configurations in which the subassembly 119 of the blades 120 and pivot ring 123 are axially moveable, the head 128 of the plunger 126 can be figured with an outer diameter that is greater than an inner diameter of the pivot ring 123, so that actuation of the plunger 126 yields distal axial translation of the subassembly 119, simply by pushing against it, following rotation of the blades 120 outward, radially.

In accordance with the invention, one or more linear pivots can be provided in lieu of the pivot ring 123. Such linear pivots can be provided as stationary elements, secured to or through the body 112, or alternatively can be mounted for axial movement with respect to the body 112. Such linear pivots can be mounted tangentially or transversely, with respect to the body 112, or can be centrally mounted (e.g., transverse to and intersecting the longitudinal axis of the body 112).

Figure 9:
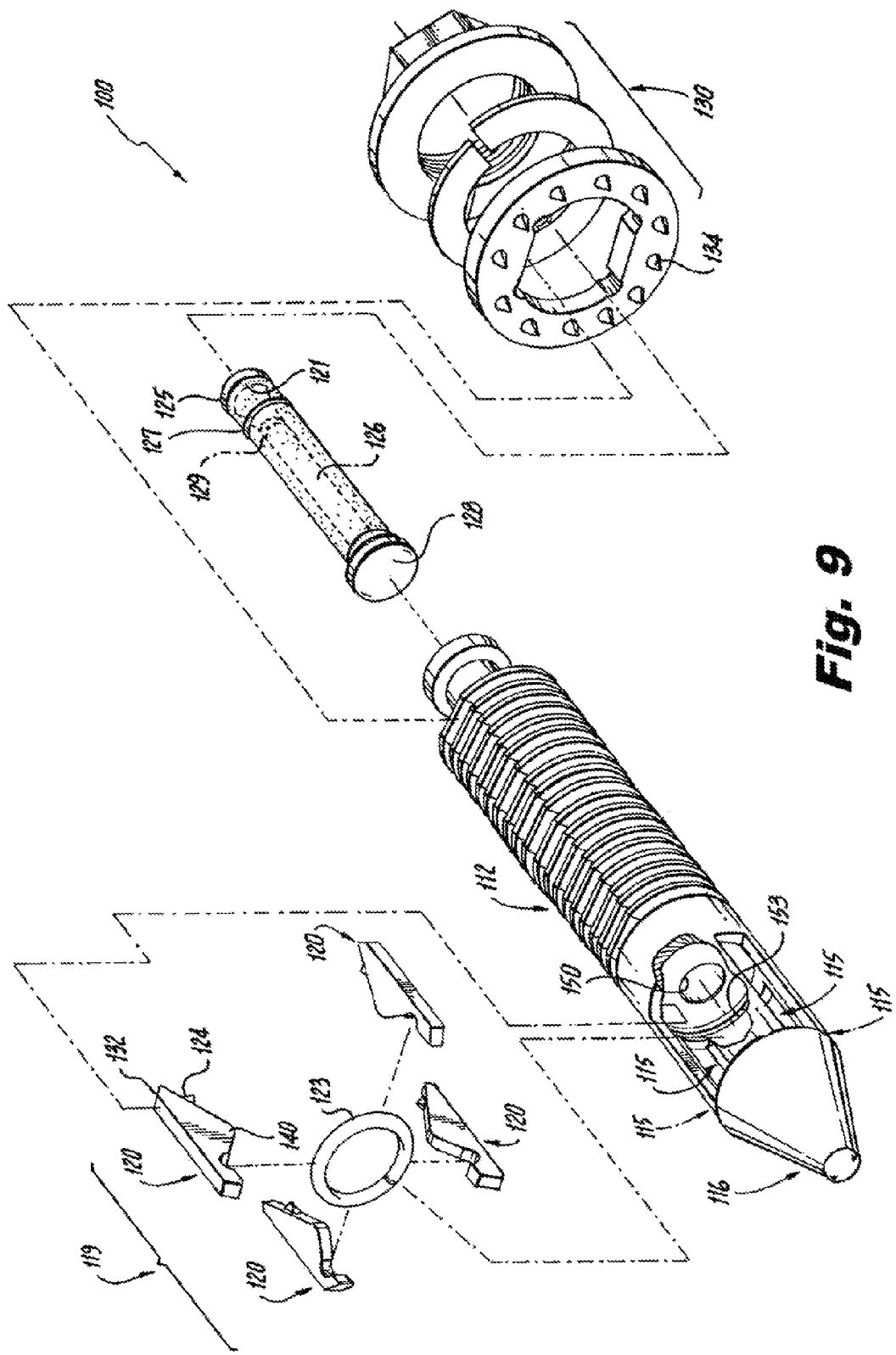
FIG. 9 is an exploded view of the implant of FIGS. 7-8, illustrating the components thereof.
Figure 12:
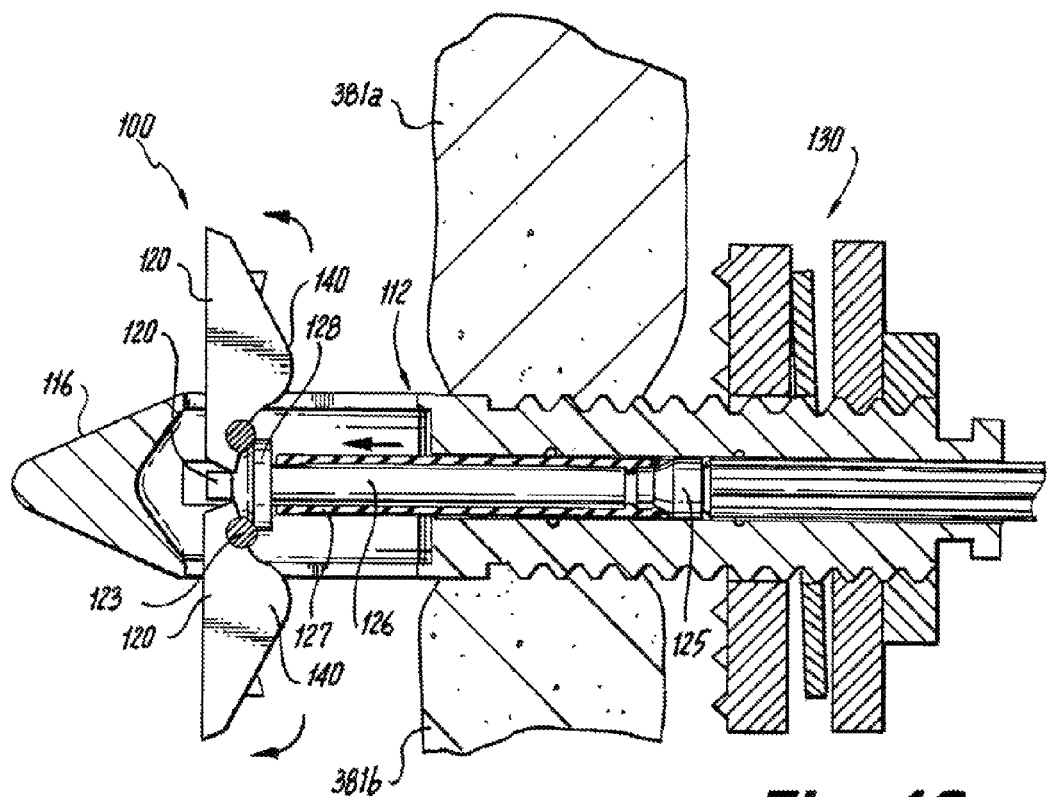
FIG. 12 is a dorsal view of the implant of FIGS. 7-9, illustrating the implant during installation, with the distal anchor elements in a deployed condition.
Figure 13:
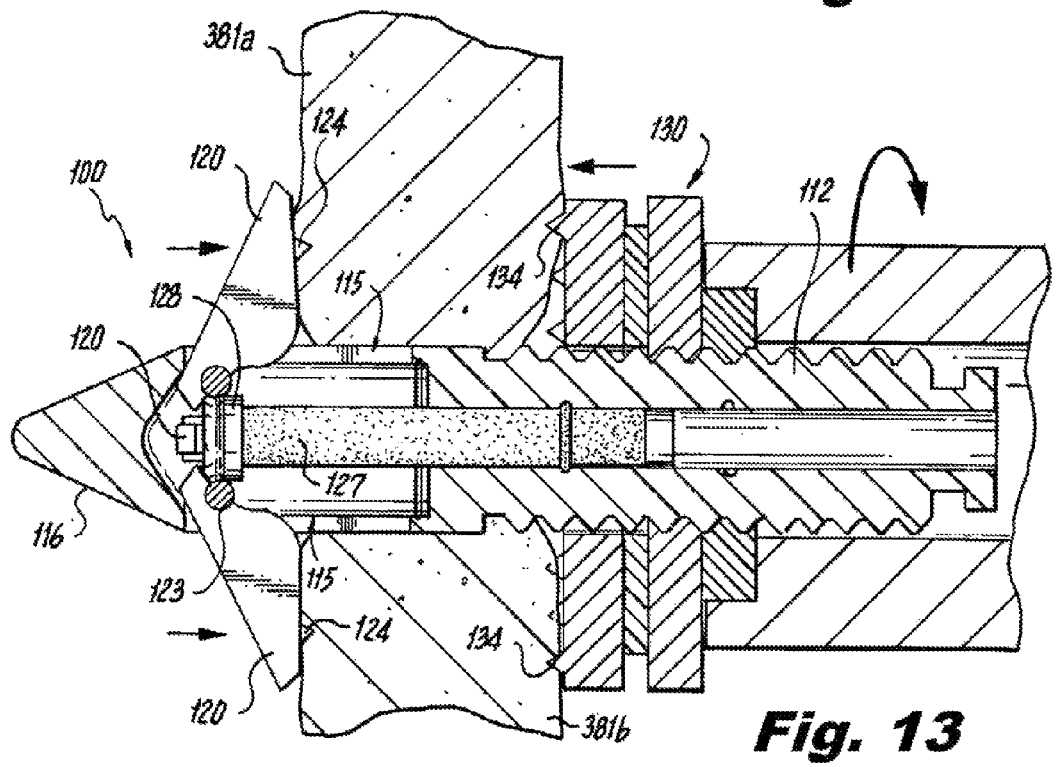
FIG. 13 is a dorsal view of the implant of FIGS. 7-9, illustrating the implant with a proximal anchor element urged distally, causing engagement of the implant with the adjacent spinous processes.
Figure 14:
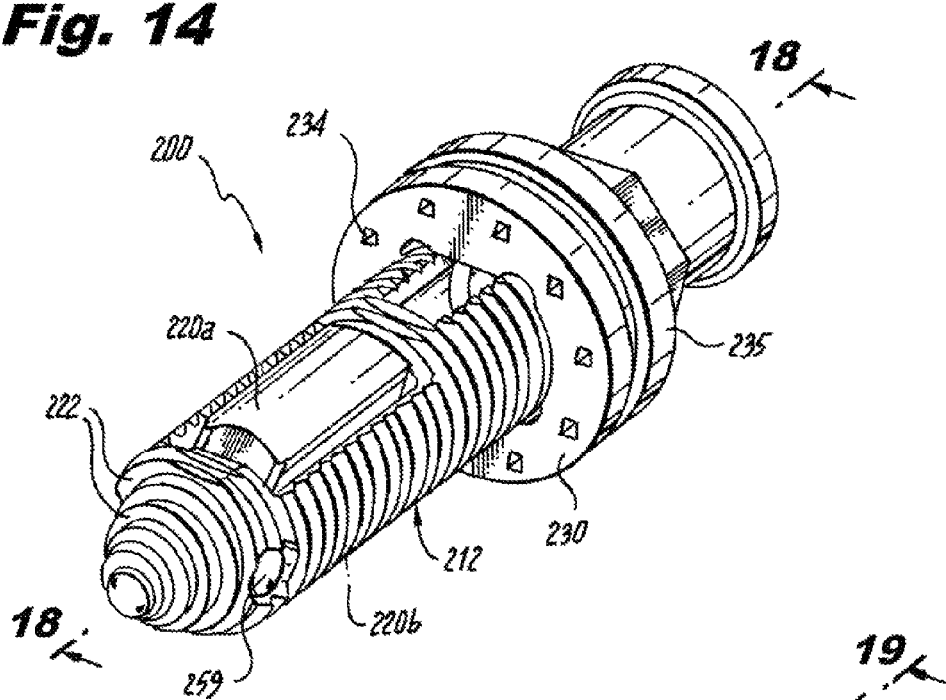
FIG. 14 is a perspective view of an interspinous process implant in accordance with a third exemplary embodiment of the invention, illustrating distal anchor elements in a stowed position.
Figure 15:
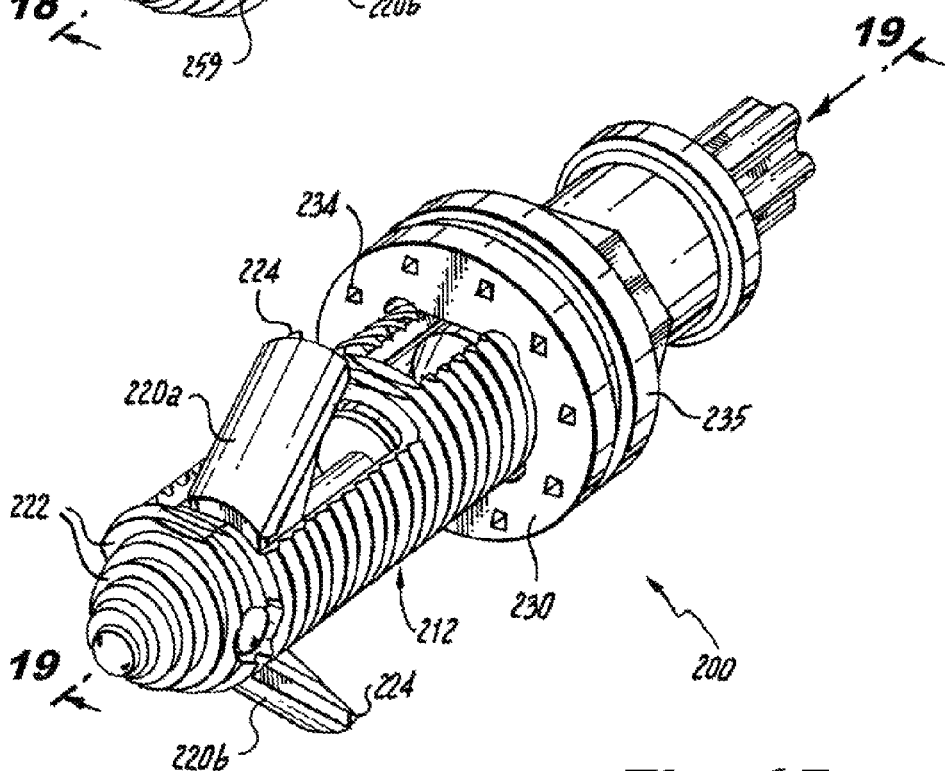
FIG. 15 is a perspective view of the implant of FIG. 14, illustrating the distal anchor elements in a deployed condition.
Figure 16:
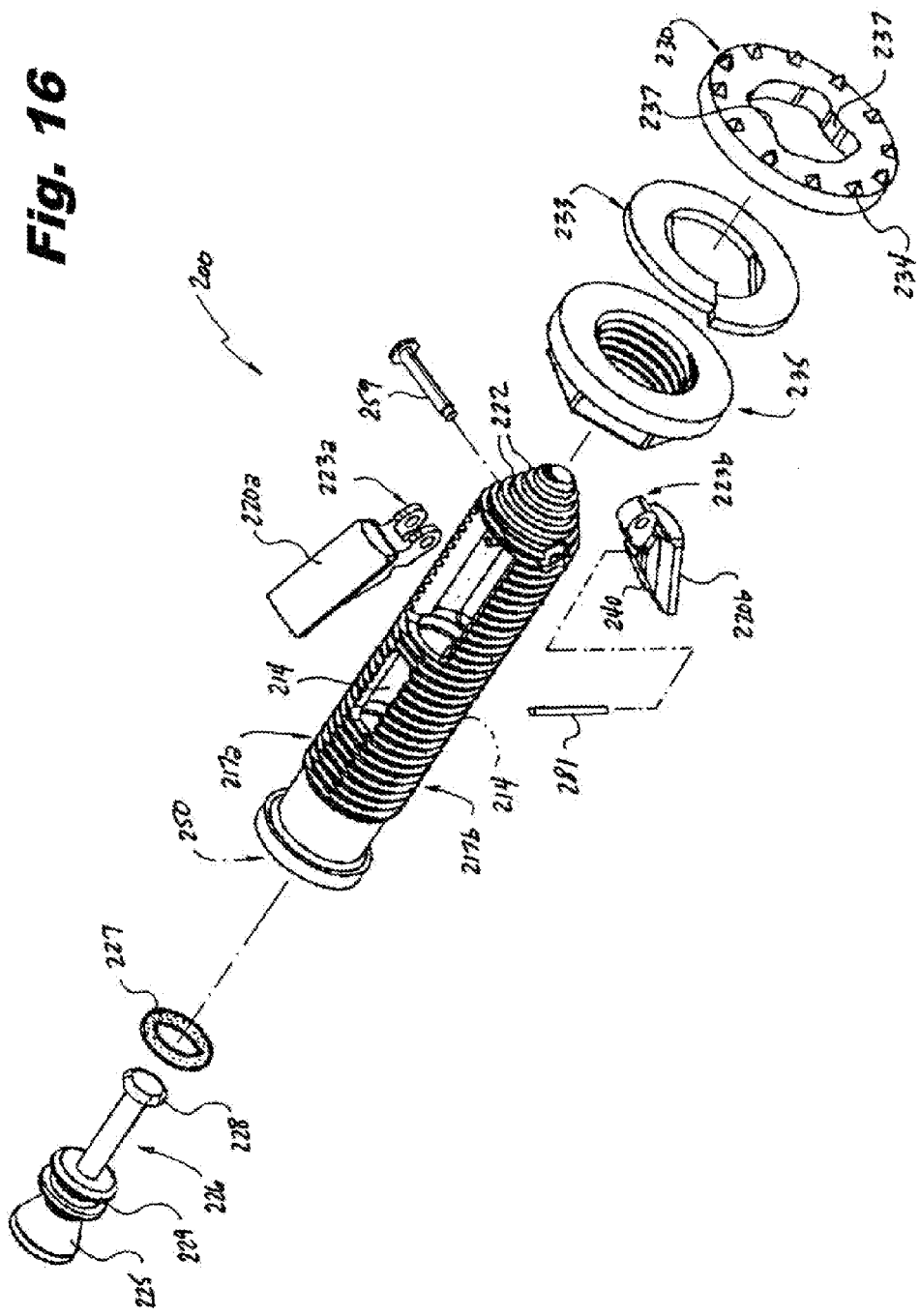
FIG. 16 is a rear exploded view of the implant of FIGS. 14-15.
Figure 17:
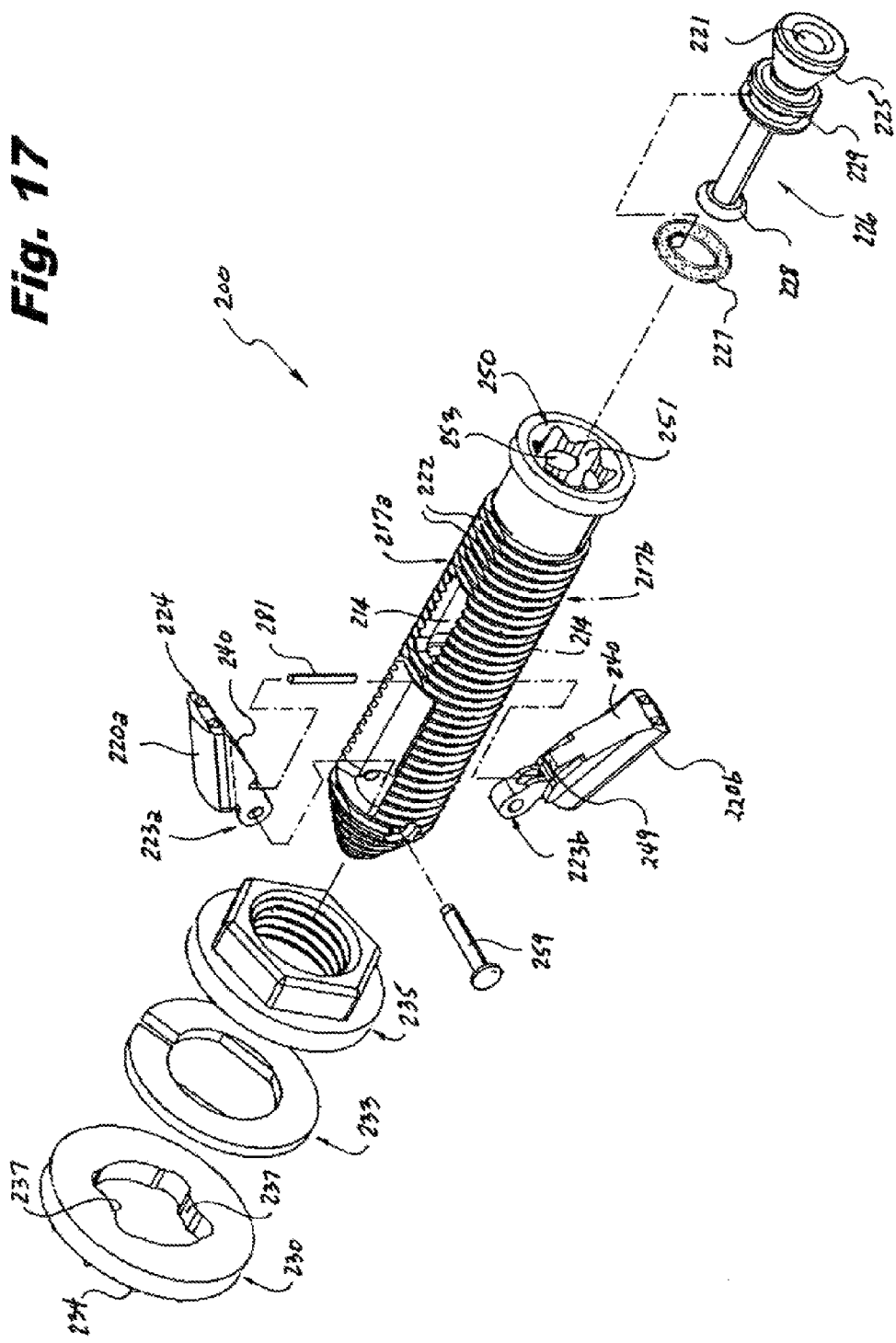
FIG. 17 is a front exploded view of the implant of FIGS. 14-15.

The plunger 126 itself can be provided with various features, including features to permit actuation thereof, and secure positioning thereof. For example, as best illustrated in FIG. 9, the plunger 126, in addition to the distal rounded head 128, can include a proximal head 125 having a proximal internal recess 121, and an angled distal surface to facilitate distal-directed urging and proximal-directed urging, respectively, applied from the proximal direction. The plunger 126 can also include a recess 129, for securely engaging a resilient catch 127. The catch 127 is configured to interface between the plunger 126 and internal surface features of the body 112, such as annular grooves or recesses. As described, the resilient catch 127 permits axial movement of the plunger 126, and in conjunction with the above-described internal surface features of the body 112, defined positions at which the plunger 126 is held, inhibiting unintentional movement therefrom. The catch 127 can be formed of any suitable material or configuration, such as from a resilient material, such as an elastomer, or as a resilient structure, such as a toroidal metallic coil, or a combination of these, for example. In the illustrated embodiment, as best seen in FIGS. 9, 12 and 13, the plunger 126 is overmolded with an elastomeric material. In the subsequent embodiment, a more discrete element is provided, which configuration can equally be applied to this embodiment.

As shown in FIGS. 7-13, the implant 100 is also similar to implant 10 in that the distal surface of the proximal anchor 130 can include a plurality of distally facing spikes 134 for engaging one side of the spinous processes 381a, 381b adjacent to the target interspinous process space 382 (FIGS. 10-13). In a similar fashion, the proximal facing surfaces of the blades 120 can be furnished with spikes 124 for engaging the other side of the spinous processes 381a, 381b.

Figure 10:
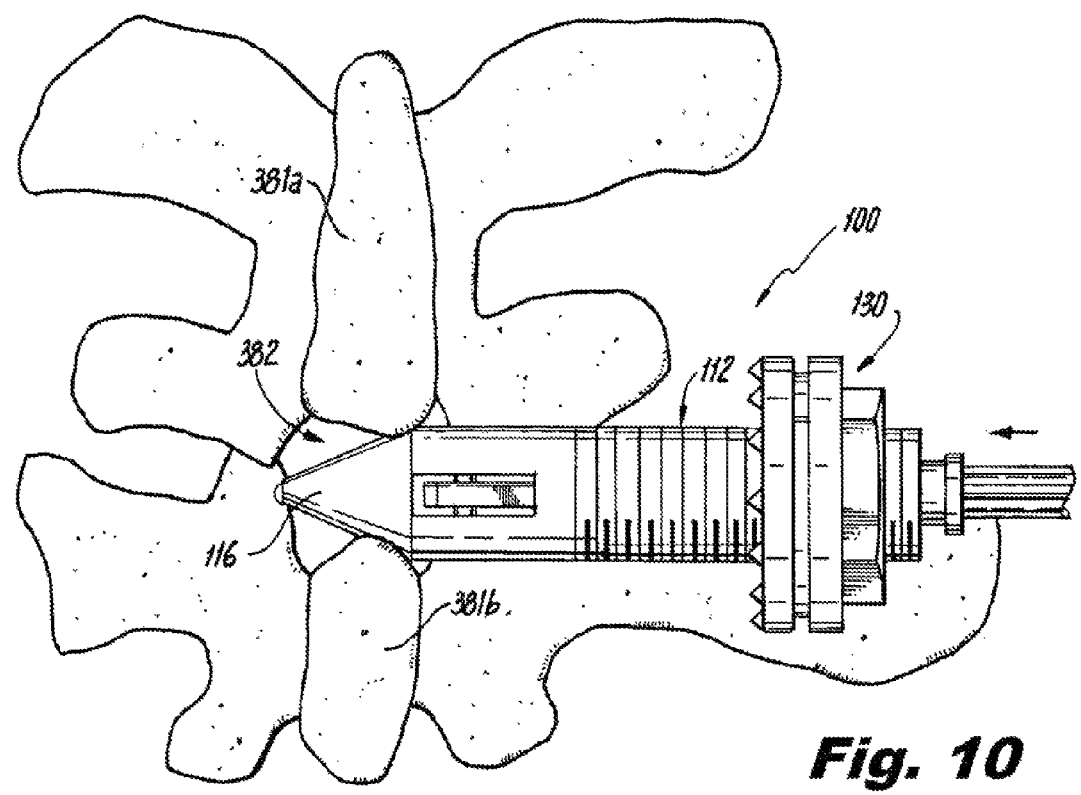
FIG. 10 is a dorsal (rear) view of the implant of FIGS. 7-9, illustrating the implant during installation into a target interspinous process space.
Figure 11:
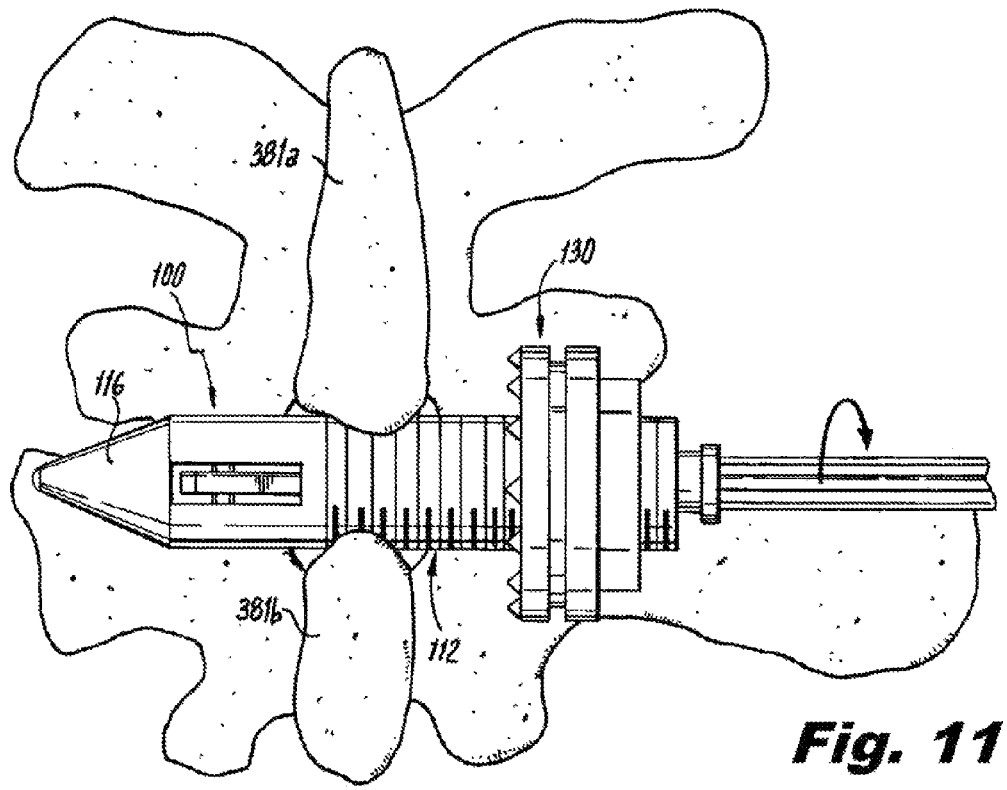
FIG. 11 is a dorsal view of the implant of FIGS. 7-9, illustrating the implant during installation, advanced to a position where distal anchor elements are unobstructed by anatomy, to allow for deployment thereof.

FIGS. 10-13 illustrate various stages during insertion and placement of the implant 100. FIG. 10 is a dorsal (rear) view of the implant 100 illustrating the implant during installation into a target interspinous process space 382. FIG. 11 is a dorsal view of the implant 100, illustrating the implant 100 during installation, advanced to a position where distal anchor elements or blades 120 are unobstructed by anatomy, allowing for deployment thereof. FIG. 12 is a dorsal view of the implant 100, illustrating the implant 100 during installation, with the distal anchor elements 120 in a deployed condition. FIG. 13 is a dorsal view of the implant 100, illustrating the implant 100 with the proximal anchor 130 urged distally, causing engagement of the implant 100 with the adjacent spinous processes 381a, 381b.

In accordance with the invention, as discussed above in connection with the embodiment of FIGS. 1-6, the implant 100 can be inserted into a target interspinous process space 382 with the blades 120 already deployed, extending outwardly from the body 112. For example, in such application, the plunger 126 is placed in a distal position where the blades 120 are deployed. The plunger 126 can be placed in a partly extended (intermediate) position, or in a fully extended position. In a partly extended position, radially-inward urging of the blades 120 causes proximal urging of the plunger 126. The plunger 126, therefore, can be provided with a stop or as spring-biased to a distal or intermediate position. If spring-biased distally, the plunger 126 will then attempt to urge the blades 120 outwardly once they are free from interference. Alternatively still, the implant 100 can be embodied such that the pivot ring 123, or other pivot arrangement, permits inward urging of the blades 120 despite placement of the plunger 126 in its fully extended position. In such an arrangement, the blades 120 pivot about the head 128 of the plunger 126, as the pivot ring 123 flexes to permit the ends 132 of the blades 120 to move inwardly.

FIGS. 14-24 illustrate an interspinous process implant 200 in accordance with a further aspect of the invention. The implant 200 includes certain features of the foregoing embodiments, where similar elements are designated with similar reference numbers as used above. The implant 200 includes a body 212, providing overall structure to the implant 200. The body 212, as illustrated, is provided with threads 222 for facilitating insertion of the implant 200 into a target interspinous process space 382 (FIGS. 20-24), as will be described in more detail below in connection with FIGS. 20-24, as well as for providing additional engagement with the anatomy of the patient in the target interspinous process space 382. Further, the threads 222 permit rotational engagement between the body 212 and a proximal nut 235, provided to securely engage the implant 200 with interspinous processes 381a, 381b adjacent the target interspinous process space 382, which will be described in more detail below. Alternatively, this implant 200, and the other implants 10, 100 of the invention can be provided without threads thereon, or with threads provided only on a portion thereof for one of the foregoing functions. That is, if desired, threads 222 can be provided only on the proximal end of the body 112, for engaging the nut 235 and not on the distal portion, or vice versa.

As with the foregoing embodiments, a distal anchor portion is provided, and in this embodiment is configured as two opposed deployable blades 220 (220a, 220b). The blades 220 are provided with a common pivot, defined by a pin 259 passing therethrough, as well as through the body 212. Use of a common pivot advantageously minimizes the space required for housing all elements within the body 212 in their stowed state, although variations from this precise configuration are possible. For example, two separate pivots can be provided for each blade 220a, 220b, still in keeping with the invention. The blades 220, as illustrated, are provided with proximally directed spikes 224 for engaging the relevant adjacent bony anatomy, such as the spinous processes 381a, 381b. The blades 220 can alternatively be provided without such spikes 224.

The blades 220a, 220b are respectively provided with hinge portions 223a, 223b for engaging the pin 259. In the illustrated embodiment, one hinge portion 223a is shaped as a clevis, while the other 223b is shaped to fit within the clevis-shaped hinge portion 223a.

In the illustrated embodiment, a plunger 226 is provided and includes a head portion 228 shaped and configured to act as a cam and cooperate with inner cam surfaces 240 formed on each of the blades 220a, 220b, as described above. As the plunger head 228 moves distally, cam surfaces 240 of the blades 220a, 200b follow the outer surface of the plunger head 228, and urge the blades 220a, 220b radially outwardly. In addition, the plunger can include, as described above, a proximal head 225 having a proximal internal recess 221, and an angled distal surface to facilitate distally-directed urging and proximal-directed urging, respectively, applied from the proximal direction. The plunger 226 can also include a recess 229, for securely engaging a resilient catch 227. The catch 227 is configured to interface between the plunger 226 and internal surface features of the body 212, such as annular grooves or recesses 254. As described, the resilient catch 227 permits axial movement of the plunger 226, and in conjunction with the above-described internal surface features of the body 212, defined positions at which the plunger 226 is held, inhibiting unintentional movement therefrom. The catch 227 can be formed of any suitable material or configuration, such as from a resilient material, such as an elastomer, or as a resilient structure, such as a toroidal metallic coil, or a combination of these, for example. The catch 227 can be, in accordance with the invention, a canted coil, such as a Bal Latch™, available from Bal Seal Engineering, Inc. of Foothill Ranch, Calif., USA.

When deployed, the blades 220 function in concert with the proximal anchor portion 230, which is axially moveable along the length of the implant 200. The nut 235 includes threads on its inner surface that engage the threads 222 provided on the outer surface of the body 212. Accordingly, rotational movement of the nut 235 yields axial movement thereof. When that axial movement is in the distal direction, the nut 235 urges the proximal anchor portion 230 distally until it abuts the bony structures (e.g. spinous processes 381a, 381b) surrounding the target interspinous process space 382. If provided, protrusions or spikes 234 on the proximal anchor portion facilitate engagement with the bone and thus stabilization of the entire vertebrae-implant construct.

As illustrated, opposed flat portions 217, comprising upper and lower flat portions 217a, 217b, respectively, guide correspondingly shaped (e.g., flat) portions 237 of the proximal anchor 230, permitting axial movement but inhibiting rotational movement thereof, during movement of the nut 235. A lock washer 233 or equivalent feature can be provided to inhibit unintentional loosening of the nut 235 following implantation and deployment of the blades 220a, 220b.

Figure 18:
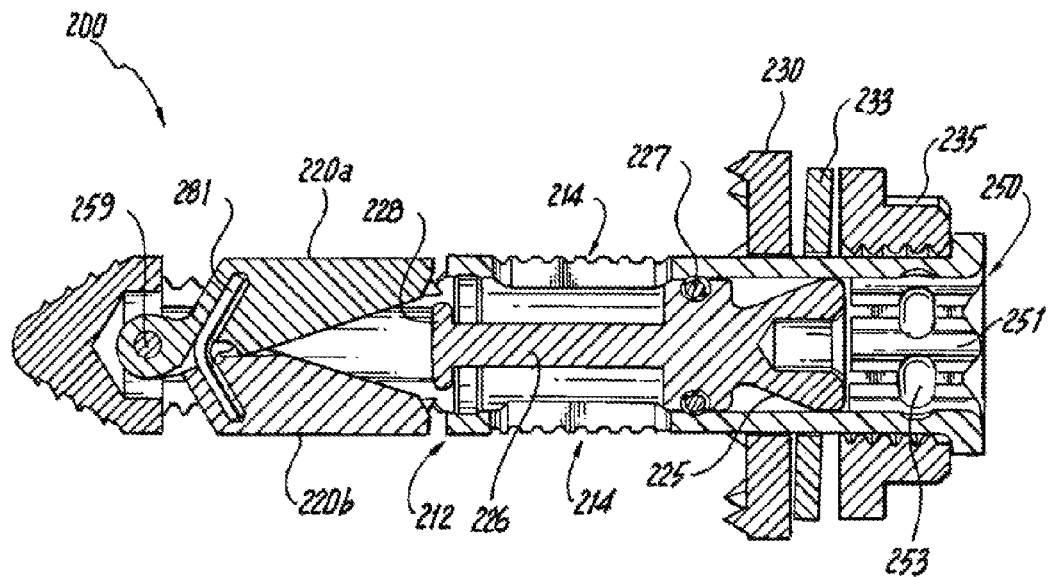
FIG. 18 is a cross-sectional view of the implant of FIGS. 14-15 taken at line 18-18 of FIG. 14, where the distal anchor elements are in a stowed position.
Figure 19:
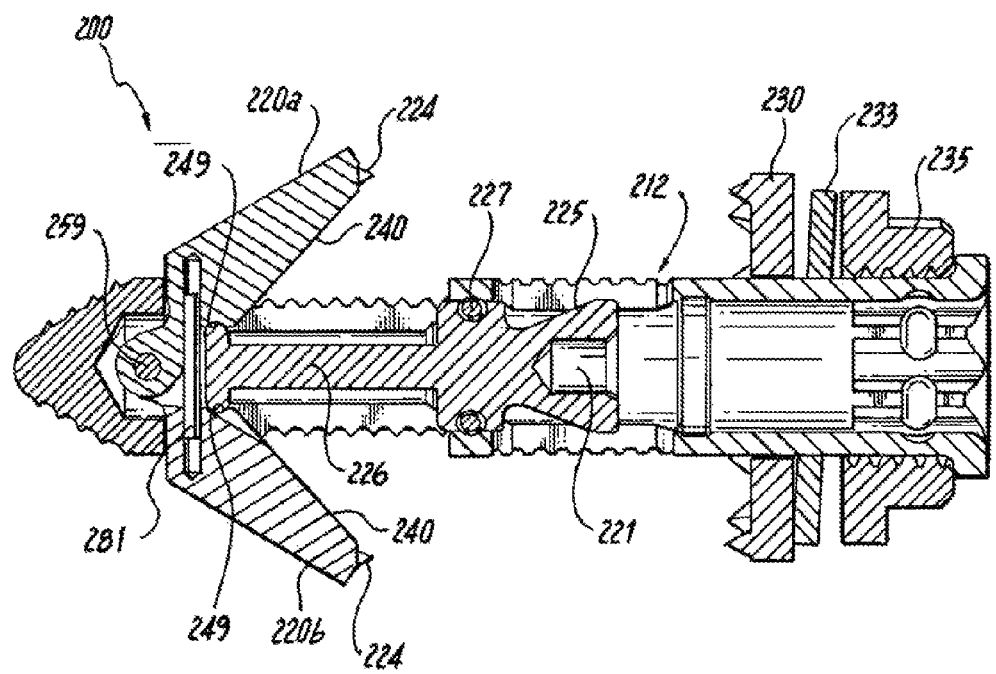
FIG. 19 is a cross-sectional view of the implant of FIGS. 14-15 taken at line 19-19 of FIG. 15, where the distal anchor elements are in a deployed position.

With reference to the cross-sectional views of FIGS. 18-19, in the illustrated embodiment, the blades 220 can be provided with an internal spring element 281, spanning between respective recess in each of the blades 220a, 220b. The spring element 281 can be provided straight to maintain the blades 220a, 220b deployed (open) normally, or alternatively, bent, to maintain the blades 220a, 220b stowed (contracted) normally. In accordance with one aspect, the spring element 281 is provided bent, and urges the blades 220a, 220b inwardly, toward the stowed position, prior to and during implantation. Thus, in connection with the plunger 226, the spring 281 serves to maintain a position of the blades 220. As illustrated, when the plunger 226 is fully extended, a head portion 228 thereof engages a corresponding detent 249 in the profile 240 of the blades 220a, 220b. The engagement of the detent 249 by the head portion 228 further ensures secure deployment of the blades 220a, 220b.

In accordance with the invention, the spring element 281 can alternatively be provided as normally straight, urging the blades 220a, 220b outwardly toward the deployed position, prior to, during and following implantation. During implantation, however, the spring element 281 permits inward rotation of the blades 220a, 220b, temporarily bending the spring element 281 in the process. Thus, during implantation the spring 281 serves to maintain a position of the blades 220a, 220b against externally-applied forces. Once placed in the target interspinous process space 382, the plunger 226 can be urged distally in order to lock the blades 220a, 220b in the deployed position. Engagement of the detent 249 by the head portion 228 of the plunger 226 further ensures maintenance of that position. The body 212 includes at its proximal end, an expanded-diameter portion 213, defining a proximal-most limit for traveling of the nut 235 and proximal anchor 230. Also in the proximal end portion, formed within the bore 250, is a shaped socket 251 for engagement with an insertion tool. As illustrated, the socket 251 is substantially hexagonal, with flat portions defined at regular angular intervals. Practicable departures from the precise configuration illustrated are possible. The shaped socket 251 facilitates mutual rotational engagement between the implant 200 and the insertion tool. Also provided in connection with the socket 251, are transverse grooves 253, which, in conjunction with a corresponding element on the insertion tool, inhibit unintentional mutual axial displacement therebetween. The corresponding element on the insertion tool can be, for example, a resiliently and optionally lockable protrusion extending laterally (i.e., radially) from the insertion tool. The lockable protrusion may be, for example, a lockable spring-loaded spherical element, for example.

As with foregoing embodiments, the implant 200 can be provided with one or more apertures 214 to permit packing of the implant, such as in the bore 250 thereof, with osteogenesis-promoting substances to facilitate bone ingrowth and/or fusion, such as demineralized bone.

Figure 20:
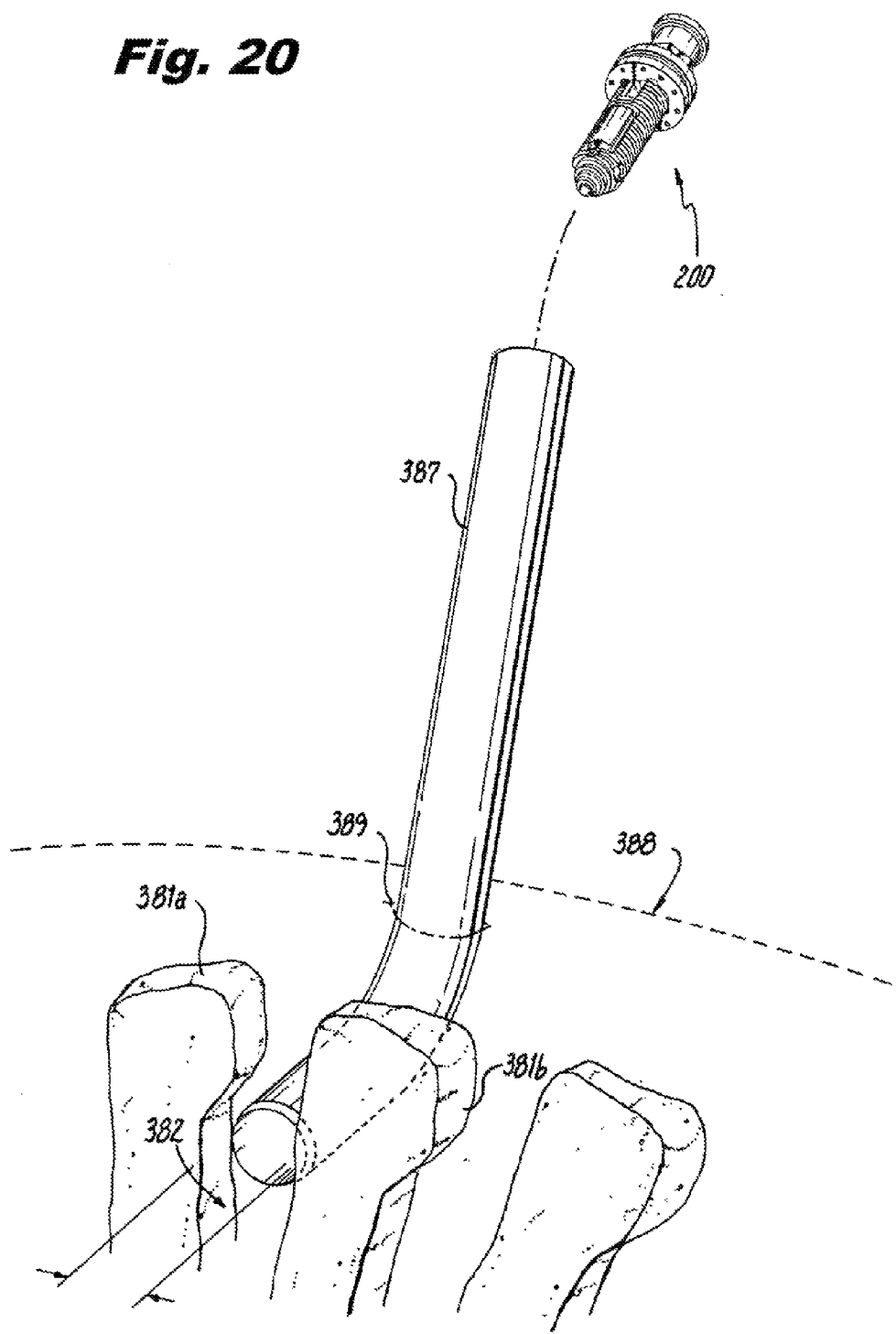
FIG. 20 is a perspective view, illustrating an implant in preparation to be installed dorsally, illustrated with the implant of FIGS. 14-15 but applicable to all embodiments of the invention.
Figure 21:
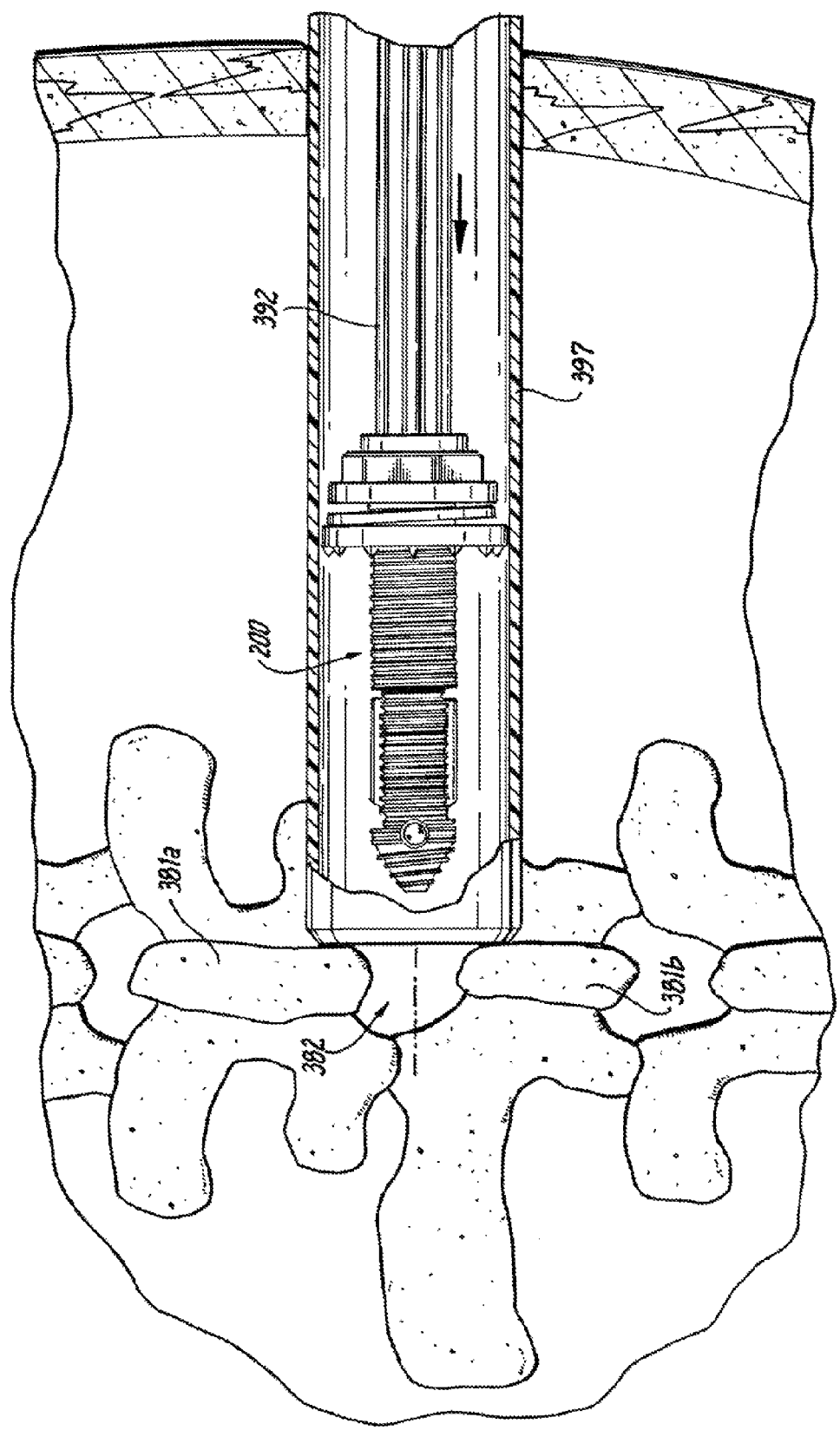
FIG. 21 is a dorsal view of an implant within an introducer tube during lateral insertion thereof, illustrated with the implant of FIGS. 14-15 but applicable to all embodiments of the invention.
Figure 22:
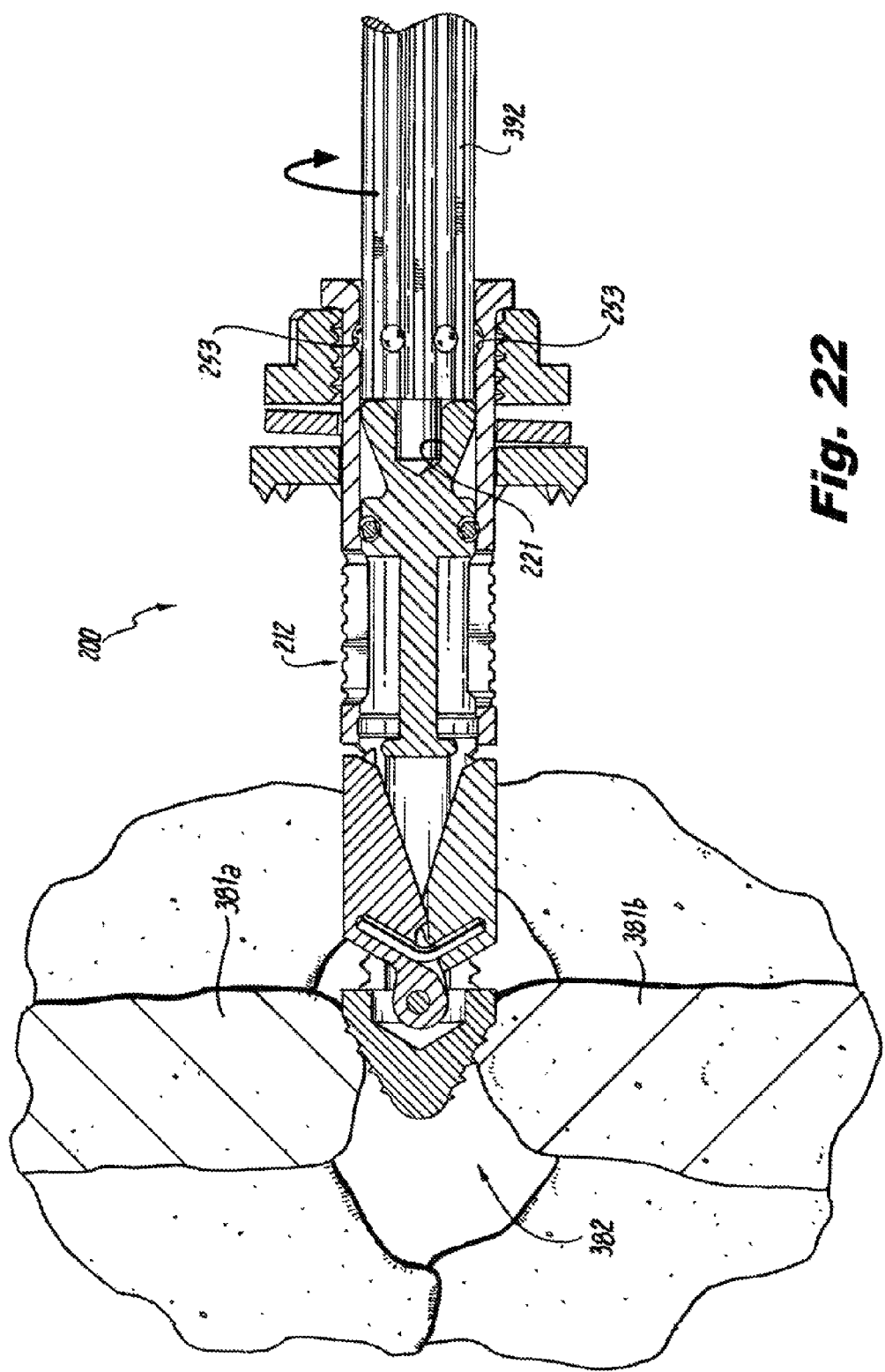
FIG. 22 is a dorsal view illustrating the implant of FIGS. 14-15, showing the implant being screwed into a target interspinous process space.
Figure 23:
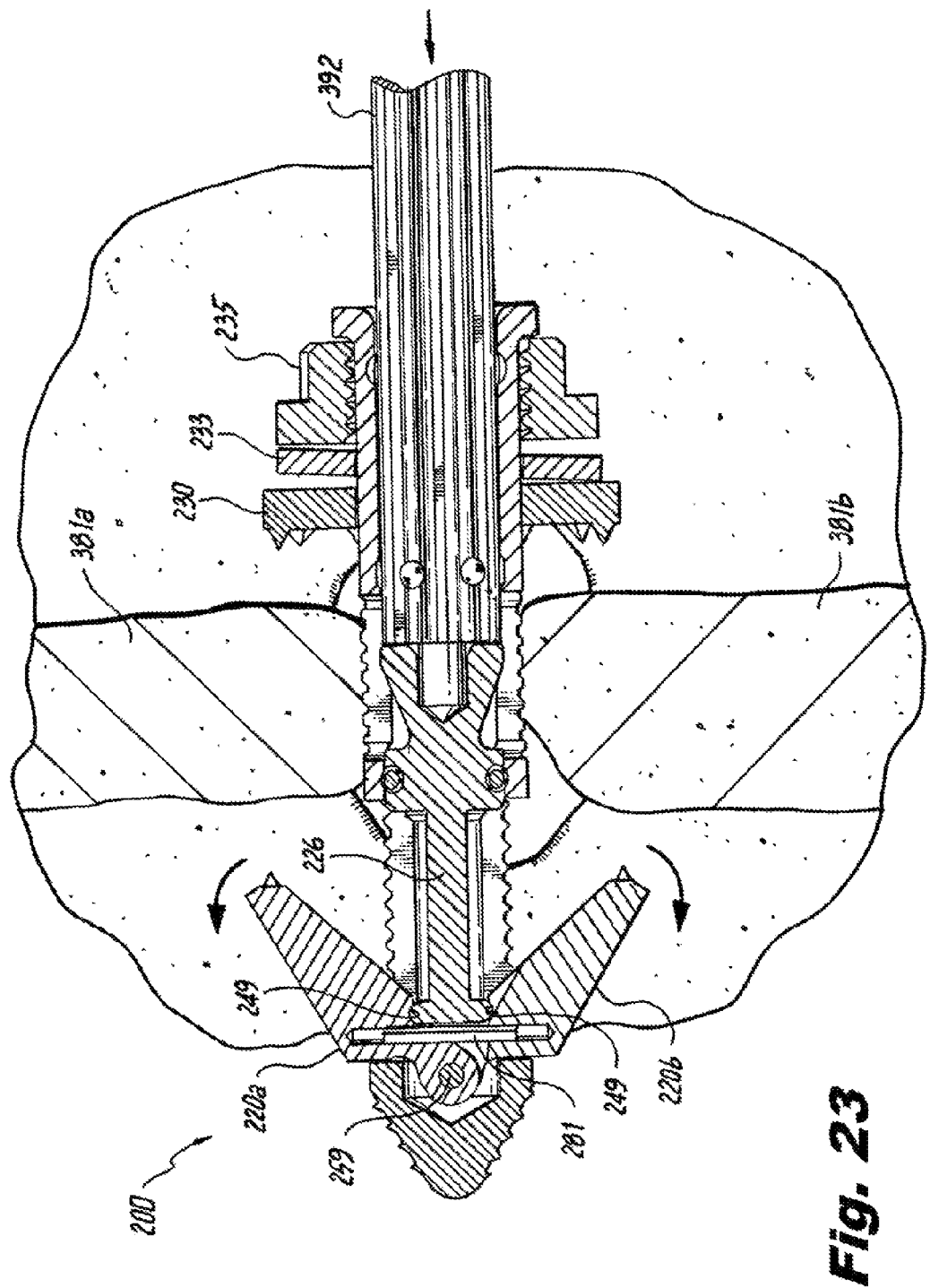
FIG. 23 is a dorsal view illustrating the implant of FIGS. 14-15, showing the implant with internal plunger urged distally, effecting deployment of the distal anchor elements.
Figure 24:
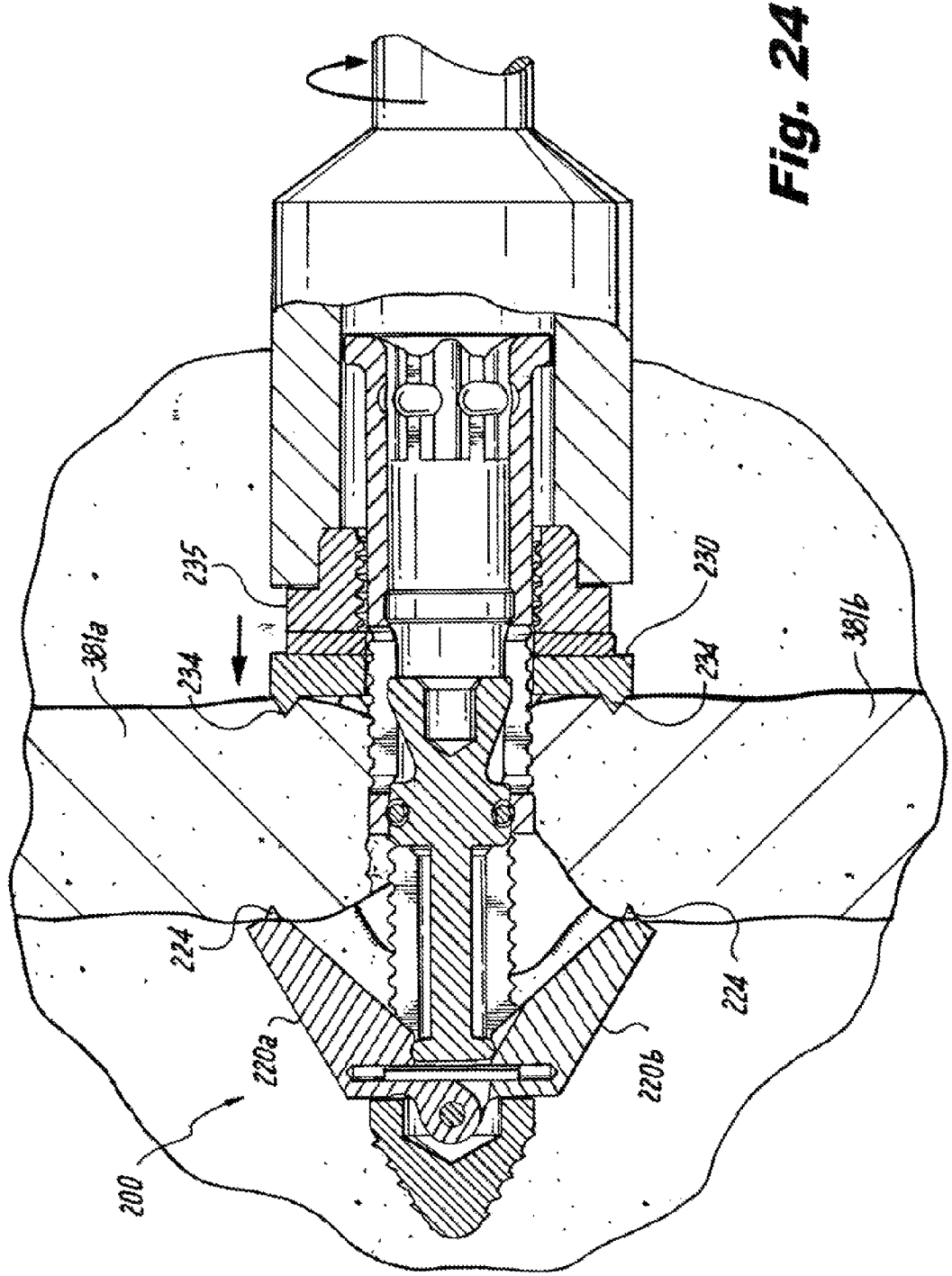
FIG. 24 is a dorsal view illustrating the implant of FIGS. 14-15, showing the proximal anchor element urged distally, engaging the adjacent spinous processes.

FIGS. 20-24 illustrate various stages during insertion and placement of the implant 200 into a target interspinous process space 382. In short, FIG. 20 is a perspective view of the implant 200, in preparation to be installed dorsally through a curved introducer tube 387, which has been inserted through an incision 389 formed through the skin 388 of a patient. FIG. 21 is a dorsal (rear) view of the implant 200, held by an elongate insertion tool 392, within a lumen of an introducer tube 397, during lateral insertion thereof. FIG. 22 is a dorsal view illustrating the implant 200, laterally advancing to the target interspinous process space 382, under application of a rotational force applied by the insertion tool 392, by virtue of the threads 222 provided on the body 212 thereof. FIG. 23 is a dorsal view illustrating the implant 200 with the internal plunger 226 urged distally, effecting deployment of the distal anchor elements—in this case, blades 220a, 220b. The nut 235 is then tightened, which urges the body 212 proximally, and thus also urges the blades 220 more securely against the adjacent bony structure, impinging the spinous processes 381a, 381b therebetween, as shown in FIG. 24, which is a dorsal view illustrating the implant 200 with the proximal anchor element 230 urged distally by the nut 235, engaging the adjacent spinous processes 281a, 281b.

More particularly, As seen in FIG. 20, a sleeve 387 is provided to facilitate insertion. The insertion methods can include use of a stylet, dilators, and the like to gain access and define a path for the sleeve 387, as will be described in more detail below. However, dorsal insertion can be accomplished as set forth in U.S. patent application Ser. No. 12/011,905, filed Jan. 30, 2008 (U.S. Pub. No. 2009/0054988), which is incorporated herein by reference in its entirety.

As illustrated, in FIG. 20, dorsal insertion of the subject implants, represented by implant 10, can be effected by forming an incision 389 through the skin 388 of a patient, at a level corresponding to a target interspinous process space 382, defined between adjacent vertebral processes 381a, 381b.

With dorsal entry illustrated in FIG. 20, the path traversed by the implant 200, and therefore also by the sleeve 387 is curved to align the path and the implant 200 with the target interspinous process space 382.

FIG. 21, in contrast, illustrates direct lateral insertion of the implant 200 into the target interspinous process space 382. In this arrangement, an incision 399 is formed in the skin 388 of a patient, and ultimately a sleeve 397 is advanced through the tissue to the target interspinous process space 382, through which the implant 200 is advanced, connected to the insertion device 392. As shown in FIGS. 22-24, which are illustrated for clarity without the sleeve 397, the implant 200 is axially rotated by way of the insertion device 392, thus threading the implant 200 into the target interspinous process space 382, distracting the adjacent spinous processes 381a, 381b, and advancing the implant 200 into its final position, generally centered with respect to the spinous processes 381a, 381b. As set forth above, distraction can be performed in advance by a separate instrument, with insertion of the implant following, and maintaining such distraction. During the rotation of the implant 200, relative rotation and axial translation between the implant 200 and the insertion device 392 is preferably inhibited by the above-mentioned features. When in position, the anchoring blades 220a, 220b can be deployed, as shown in FIG. 23. Subsequently, the nut 235 can be tightened, advancing the locking proximal anchor 230 distally into engagement with the spinous processes 381a, 381b.

Subsequently, one or more osteogenesis promoting substances can be packed in and/or around the implant 200 to promote bone ingrowth and/or spinal fusion, if desired.

A separate tap can be used in the target interspinous process space 382 before the insertion of the implant 200, or as mentioned above, the implant 200 can be provided with features that provide self-tapping capability.

Methods of lateral insertion of the spinal implant 200 into a target interspinous process space 382 can include, following forming the incision 399, inserting a stylet (not illustrated) through the incision 399, laterally to the target interspinous process space 382, preferably using an internal imaging technique, such as fluoroscopy.

Insertion of the stylet forms an entry path, along which one or more dilators can be sequentially advanced, in order to dilate soft tissues between the incision and the target interspinous process space 382. The sleeve 397 can then be advanced through the entry path. After inserting the sleeve 397, a distractor, which can be a tap (e.g., a graduated tap), can then be inserted and advanced into the target interspinous process space 382, to tap and gradually distract the adjacent spinous processes 381a, 381b and/or help determine an appropriate size of implant to be inserted.

Following selection of an implant 200 having a size appropriate for a desired amount of interspinous distraction, the implant 200 can be inserted, held by the insertion device 392, advanced through the sleeve 397, up to the target interspinous process space 382, after which the implant 200 can be inserted into the target interspinous process space 382. In the case of threaded implants, rotational motion is applied to advance the implant 200 and, if not already distracted, to distract the adjacent spinous processes 381a, 381b. In the case of non-threaded implants, laterally-directed pressure can be applied until the implant 300 is in the desired position, after which any proximal and/or distal engagement elements can be deployed.

Many of the primary structural components of the implant devices described herein are preferably formed from biological and/or biocompatible materials, including metal, ceramic, polymeric and/or composite materials that can be selected to have a modulus of elasticity that is substantially similar to that of bone, for example, polyetheretherketone thermoplastic (PEEK), machined bone, a titanium alloy or stainless steel, for example.

While the apparatuses and methods of subject invention have been shown and described with reference to preferred embodiments, it is to be understood that any feature described in connection with one embodiment can be advantageously applied to other embodiments of the invention, even if not explicitly described in connection therewith, if such feature(s) are not mutually exclusive with other features of such embodiment. Nevertheless, those skilled in the art will readily appreciate that further changes or modifications may be made to devices and methods of the present invention without departing from the spirit and scope thereof.

What is claimed is:

1. A method of percutaneously performing interspinous process decompression, comprising the steps of:
   a) providing a spinal implant having an elongated body dimensioned and configured to function as a spacer, for placement in a target interspinous process space, between two adjacent spinous processes, wherein an outer surface of the body is threaded, a distal anchor associated with a distal end of the body, and a proximal anchor mounted for longitudinal movement along the body between a first position spaced apart from the head and a second position approximated with the distal end, the proximal anchor being adapted to engage the two adjacent spinous processes, in conjunction with the distal anchor, wherein the proximal anchor includes an axially slideable plate and a nut threaded to the threaded outer surface of the body for axial movement of the proximal anchor by rotational movement of the nut;
   b) forming an incision in a patient's skin, lateral from a target interspinous process space, in which the implant is to be placed;
   c) inserting a stylet through the incision, laterally to the target interspinous process space, using an internal imaging technique, to form an entry path;
   d) inserting one or more dilators, sequentially, along the entry path to dilate soft tissues between the incision and the target interspinous process space;
   e) inserting a sleeve through the entry path;
   f) selecting an implant having a size appropriate for a desired amount of interspinous distraction;
   g) inserting the implant, held by an insertion device, through the sleeve, up to the target interspinous process space; and
   h) advancing the implant into the interspinous process space,
   wherein the inserting step includes inserting a tapered end of the distal anchor between two adjacent spinous processes such that a trailing skirt section of the tapered end transitions between a radially expanded condition to a radially compressed condition.

2. The method of claim 1, wherein the step of advancing includes advancing the trailing skirt section beyond the spinous processes such that the trailing skirt section is urged back into the radially expanded condition.

* * * * *